US005658902A

United States Patent [19]

Ahn et al.

[11] Patent Number: 5,658,902
[45] Date of Patent: Aug. 19, 1997

[54] QUINAZOLINES AS INHIBITORS OF ENDOTHELIN CONVERTING ENZYME

[75] Inventors: Kyunghye Ahn; Xue-Min Cheng; Annette Marian Doherty; Edward Faith Elslager; Brian Kornberg; Chitase Lee; Daniele Leonard; Sham Nikam; Leslie Morton Werbel, all of Ann Arbor, Mich.

[73] Assignee: Warner-Lambert Company, Morris Plains, N.J.

[21] Appl. No.: 363,104

[22] Filed: Dec. 22, 1994

[51] Int. Cl.$^6$ ............... C07D 401/12; C07D 403/12; C07D 405/12; A61K 31/505

[52] U.S. Cl. ............ 514/234.8; 514/259; 514/254; 514/255; 514/228.2; 514/212; 544/293; 544/116; 544/284; 544/238; 544/357; 544/296; 544/62; 540/600; 540/582

[58] Field of Search ............ 544/293, 116, 544/284, 62; 514/259, 234.8, 260, 228.2, 212; 540/600, 582

[56] References Cited

U.S. PATENT DOCUMENTS

| 3,184,462 | 5/1965 | Homer et al. ............ 260/256.4 |
| 3,340,260 | 9/1967 | Morton et al. ............ 260/247.1 |
| 3,470,182 | 9/1969 | Hardtmann et al. ............ 260/256.4 |
| 3,997,538 | 12/1976 | Alaimo ............ 239/94 |
| 4,788,199 | 11/1988 | Benavides et al. ............ 514/259 |
| 5,145,843 | 9/1992 | Arnold et al. ............ 514/63 |
| 5,187,168 | 2/1993 | Primeau et al. ............ 514/259 |
| 5,240,940 | 8/1993 | Arnold et al. ............ 514/312 |

FOREIGN PATENT DOCUMENTS

| 646856 | 10/1964 | Belgium . |
| 0436189 | 7/1991 | European Pat. Off. . |
| 0518299 | 12/1992 | European Pat. Off. . |
| 607439A1 | 4/1993 | European Pat. Off. . |
| 0579496 | 1/1994 | European Pat. Off. . |
| 1800709 | 12/1969 | Germany . |
| 0578556 | 8/1976 | Switzerland . |
| 466233 | 11/1975 | U.S.S.R. . |
| 857362 | 12/1960 | United Kingdom . |
| 956254 | 4/1964 | United Kingdom . |
| 1199768 | 7/1970 | United Kingdom . |
| 8401151 | 3/1984 | WIPO . |
| 9213944 | 8/1992 | WIPO . |
| 9319050 | 9/1993 | WIPO . |

OTHER PUBLICATIONS

Takase, Y. et al. *Chemical Abstract Services*, CA 119:203427 (1993).
Patterson, S.E., et al., *J. Heterocycl. Chem* (Jul. 1992), 29(4) 703–6.
Browns, D.J., et al., *Aust. J. Chem.* (1985), 38(3), 467–74.
Genther, C.S., et al., *J. Med. Chem.* (1977), 20(2), 237–43.
PCT International Search Report, PCT/US 95/15366, Jun. 1996.
Chemical Abstracts, vol. 93, No. 21, 1980, abstract No. 204585z.
Chemical Abstracts, vol. 90, No. 5, 1979, abstract No. 198861f.
Chemical Abstracts, vol. 83, No. 28, 1975, abstract No. 58869v.
Sandoz, AG Derwent Abstract No. 76-72258x (1976).

*Primary Examiner*—Mukund J. Shah
*Assistant Examiner*—King Lit Wong
*Attorney, Agent, or Firm*—Francis J. Tinney

[57] ABSTRACT

Novel quinazoline inhibitors of endothelin converting enzyme are described, as well as methods for the preparation and pharmaceutical compositions of the same, which are useful in treating elevated levels of endothelin and in controlling hypertension, myocardial infarction and ischemia, metabolic, endocrinological, and neurological disorders, congestive heart failure, endotoxic and hemorrhagic shock, septic shock, subarachnoid hemorrhage, arrhythmias, asthma, acute and chronic renal failure, cyclosporin-A induced nephrotoxicity, angina, gastric mucosal damage, ischemic bowel disease, cancer, pulmonary hypertension, preeclampsia, atherosclerotic disorders including Raynaud's disease and restenosis, cerebral ischemia and vasospasm, and diabetes.

13 Claims, No Drawings

QUINAZOLINES AS INHIBITORS OF ENDOTHELIN CONVERTING ENZYME

BACKGROUND OF THE INVENTION

The present invention relates to novel quinozoline inhibitors of endothelin converting enzyme useful as pharmaceutical agents, to methods for their production, to pharmaceutical compositions which include these compounds and a pharmaceutically acceptable carrier, and to pharmaceutical methods of treatment. More particularly, the novel compounds of the present invention are inhibitors of endothelin converting enzyme useful in treating elevated levels of endothelin and in controlling hypertension, myocardial infarction and ischemia, metabolic, endocrinological, and neurological disorders, congestive heart failure, endotoxic and hemorrhagic shock, septic shock, subarachnoid hemorrhage, arrhythmias, asthma, acute and chronic renal failure, cyclosporin-A induced nephrotoxicity, angina, gastric mucosal damage, ischemic bowel disease, cancer, pulmonary hypertension, preeclampsia, atherosclerotic disorders including Raynaud's disease and restenosis, cerebral ischemia and vasospasm, and diabetes.

Endothelin-1 (ET-1), a potent vasoconstrictor, is a 21 amino acid bicyclic peptide that was first isolated from cultured porcine aortic endothelial cells. Endothelin-1, is one of a family of structurally similar bicyclic peptides which include; ET-2, ET-3, vasoactive intestinal contractor (VIC), and the sarafotoxins (SRTXs). The unique bicyclic structure and corresponding arrangement of the disulfide bridges of ET-1, which are the same for the endothelins, VIC, and the sarafotoxins, has led to significant speculation as to the importance of the resulting induced secondary structure to receptor binding and functional activity. ET-1 analogs with incorrect disulfide pairings exhibit at least 100-fold less vasoconstrictor activity.

Endothelin-1 is generated from a 203 amino acid peptide known as preproendothelin by an unknown dibasic endopeptidase. This enzyme cleaves the prepropeptide to a 38 (human) or 39 (porcine) amino acid peptide known as big endothelin or proendothelin. Big ET is then cleaved by an enzyme, known as endothelin converting enzyme or ECE, to afford the biologically active molecule ET-1. Big ET is only 1% as potent as ET-1 in inducing contractile activity in vascular strips but it is equally potent in vivo at raising blood pressure, presumably by rapid conversion to ET-1 (Kimura S, Kasuya Y, Sawamura T, et al., "Conversion of big endothelin-1 to 21-residue endothelin-1 is essential for expression of full vasoconstrictor activity: Structure-activity relationship of big endothelin-1," *J Cardiovasc Pharmacol* 1989;13:S5). There have been numerous reports describing possible proteases in both the cytoplasm and membrane bound cellular fractions of endothelial cells (Ikegawa R, Matsumura Y, Takaoka M, et al., "Evidence for pepstatin-sensitive conversion of porcine big endothelin-1 to endothelin-1 by the endothelial cell extract," *Biochem Biophys Res Commun* 1990;167:860; Sawamura T, Kimura S, Shinmi O, et al., "Characterization of endothelin converting enzyme activities in soluble fraction of bovine cultured endothelial cells," *Biochem Biophys Res Commun* 1990;169:1138; Sawamura T, Shinmi O, Kishi N, et al., "Analysis of big endothelin-1 digestion by cathepsin D." *Biochem Biophys Res Commun* 1990;172:883; Shields PP, Gonzales TA, Charles D, et al., "Accumulation of pepstatin in cultured endothelial cells and its effect on endothelin processing," *Biochem Biophys Res Commun* 1991;177:1006; Matsumura Y, Ikegawa R, Tsukahara Y, et al., "Conversion of big endothelin-1 to endothelin-1 by two types of metalloproteinases derived from porcine aortic endothelial cells," *FEBS Lett*, 1990;272:166; Sawamura T, Kasuya Y, Matsushita SN, et al., "Phosphoramidon inhibits the intracellular conversion of big endothelin-1 to endothelin-1 in cultured endothelial cells," *Biochem Biophys Res Commun* 1991;174:779; Takada J, Okada K, Ikenaga T, et al., "Phosphoramidon-sensitive endothelin-converting enzyme in the cytosol of cultured bovine endothelial cells," *Biochem Biophys Res Commun* 1991;176:860; Ahn K, Beningo K, Olds G, Hupe D, "Endothelin-converting enzyme from bovine and human endothelial cells," *J Vasc Res* 1991;29:76, 2nd International symposium on endothelium-derived vasoactive factors). Many groups have chosen to isolate ECE from endothelial cells of various species, since endothelin is known to be synthesized and secreted by this cell type. It was initially reported that two types of protease activity were present in porcine or bovine endothelial cells that could cause conversion of big ET to ET in vitro (Ikegawa R, supra; Sawamura T, supra; Matsumura Y, supra; Takada J, supra; Ahn K, supra). However, it was subsequently found that the aspartic protease activity from porcine endothelial cells, thought to be predominantly cathepsin D, also caused further degradation of ET-1 and was therefore unlikely to be the true ECE (Sawamura T, supra). Moreover, human cathepsin D also causes rapid degradation of ET-1. In addition, there has been one study showing that the intracellular accumulation of pepstatin, an aspartic protease inhibitor, did not inhibit ET-1 production in cultured bovine aortic endothelial cells (Shields PP, supra). Stronger evidence that ECE is in fact a neutral metalloprotease has appeared (Matsumura Y, supra; Sawamura T, supra; Takada J, supra; Ahn K, supra) and, recently, rat and bovine ECE genes have been cloned and expressed, confirming that ECE is a phosphoramidon sensitive metalloprotease. (Shimada, K., Tanzawa, K., *J. Biol. Chem.* 1994, 269, 18275) (Dong, X., Emoto, N., Giaid, A., Slaughter, C., Kaw, S., deWit, D., Yanagisawa, M., *Cell* 1994, 78, 1–20). However, the non-specific metalloproteinase inhibitor, phosphoramidon, has been shown to inhibit the intracellular conversion of big ET-1 to ET-1 in cultured vascular endothelial cells and smooth muscle cells (Sawamura T, supra).

ET-converting activity has been detected in both the membranous and cytosolic fractions of cultured porcine, bovine, and human endothelial cells (Matsumura Y, supra). Micromolar concentrations of phosphoramidon have been shown to block the pressor response of big ET both in vitro and in vivo (Takada J, supra; Fukuroda T, Noguchi K, Tsuchida S, et al., "Inhibition of biological actions of big endothelin-1 by phosphoramidon," *Biochem Biophys Res Commun* 1990;172:390; Matsumura Y, Hisaki K, Takaoka M, Morimoto S, "Phosphoramidon, a metalloproteinase inhibitor, suppresses the hypertensive effect of big endothelin-1," *Eur J Pharmacol* 1990;185:103; McMahon EG, Palomo MA, Moore WM, et al., "Phosphoramidon blocks the pressor activity of porcine big endothelin-1-(1–39) in vivo and conversion of big endothelin-1-(1–39) to endothelin-1-(1–21) in vitro," *Proc Natl Acad Sci USA* 1991;88:703). It has recently been reported that phosphoramidon is able to inhibit vasoconstrictor effects evoked by intravenous injections of big ET-1 in anaesthetized pigs, but did not have any effect on the plasma ET-1 level (Modin A, Pernow J, Lundberg JM, "Phosphoramidon inhibits the vasoconstrictor effects evoked by big endothelin-1 but not the elevation of plasma endothelin-1 in vivo," *Life Sci* 1991;49:1619). It should be noted that phosphoramidon is a rather general metalloproteinase inhibitor and clearly the discovery of specific ECE inhibitors such as those described in the present invention is important.

The importance of ECE inhibitors is supported further by more recent reports. Several studies demonstrating the inhibition of ECE by metalloprotease inhibitors like phosphoramidon in vitro have been published (Doherty, A. D., Endothelin: A New Challenge. *J. Med. Chem.* 1992, 35, 1493; Simonson, J. S., Endothelins: Multifunctional Renal Peptides. *Physiological Reviews.* 1993, 73, 375; Opgenorth, T. J.; Wu-Wong, J. R.; Shiosaki, K. Endothelin Converting Enzymes, *FASEB. J.* 1992, 6, 2653–2659; Pollock, D. M.; Opgenorth, T. J. Evidence for metalloprotease involvement in the in vivo effects of big endothelin-1 *Am. J. Physiol.* 1991, 261, 257–263). These studies have also been followed up by in vivo studies where the effects Of ET in physiological conditions have been blocked by ECE inhibitors. For example, several reports have demonstrated that phosphoramidon ($IC_{50}$=~1 µM) inhibits ECE in vitro. These results were supported by in vivo studies where phosphoramidon blocked the vasoconstrictive effects of ET. In ganglion-blocked anesthetized rats the pressor response of big ET-1 was blocked by phosphoramidon in a dose-dependent manner (McMahon, E. G.; Palomo, M. A.; Moore, W. M. Phosphoramidon blocks the pressor activity of big endothelin (1–39) and lowers blood pressure in spontaneously hypertensive rats. *J. Cardiovasc, Pharmacol.* 1991, 17 (Suppl. 17), S29–S33; McMahon, E. G.; Palomo, M. A.; Moore, W. M.; McDonald, J. F.; Stern, M. K. Phosphoramidon blocks the pressor activity of porcine big endothelin-1-(1–39) in vivo and conversion of big endothelin-1-(1–39) to endothelin-1-(1–21) in vitro *Proc. Natl. Acad. Sci (USA)*, 1991, 88, 703–707). Phosphoramidon was also shown to inhibit the effects of big ET-1 in the microvasculature of anesthetized hamsters and has also been used to suppress the lethality induced by the intravenous infusion of big ET-1 (Lawerence, E.; Brain, S. D. Big endothelin-1 and big endothelin-3 are constrictor agents in the microvasculature: evidence for the local phosphoramidon-sensitive conversion of big endothelin-1. *Eur. J. Pharmacol.* 1993, 233, 243–250). In all cases it was shown that phosphoramidon inhibited the effects of big ET-1 and not ET-1 indicating that it was not behaving as a receptor antagonist. Intracisternal administration of big ET-1 in anesthetized dogs decreased the caliber of the basilar artery on the angiogram and systemic arterial pressure was also elevated. These effects were blocked by phosphoramidon (Shinyama, H.; Uchida, T.; Kido, H.; Hayashi, K.; Watanabe, M.; Matsumura, Y.; Ikegawa, R.; Takaoka, M.; Morimoto, S. Phosphoramidon inhibits the conversion of intracisternally administered big endothelin-1 to endothelin-1. *Biochem Biophys Res Commun* 1991, 178, 24–30). Similar enzyme inhibitory activity has been reported in the studies involving phosphoramidon sensitive inhibition of hemodynamic actions of big ET-1 in rat brain (Hashim, M. A.; Tadepalli. Functional evidence for the presence of a phosphoramidon-sensitive enzyme in rat brain that converts big endothelin-1 to endothelin-1. *Life Sci.* 1991, 49, 207–211).

Endothelin is involved in many human disease states.

Several in vivo studies with ET antibodies have been reported in disease models. Left coronary artery ligation and reperfusion to induce myocardial infarction in the rat heart, caused a four- to sevenfold increase in endogenous endothelin levels. Administration of ET antibody was reported to reduce the size of the infarction in a dose-dependent manner (Watanabe T, et al., "Endothelin in Myocardial Infarction," *Nature* (Lond.) 1990;344:114). Thus, ET may be involved in the pathogenesis of congestive heart failure and myocardial ischemia (Margulies KB, et al., "Increased Endothelin in Experimental Heart Failure," *Circulation* 1990;82:2226).

Studies by Kon and colleagues using anti-ET antibodies in an ischemic kidney model, to deactivate endogenous ET, indicated the peptide's involvement in acute renal ischemic injury (Kon V, et al., "Glomerular Actions of Endothelin In vivo," *J Clin Invest* 1989;83:1762). In isolated kidneys, preexposed to specific antiendothelin antibody and then challenged with cyclosporine, the renal perfusate flow and glomerular filtration rate increased, while renal resistance decreased as compared with isolated kidneys preexposed to a nonimmunized rabbit serum. The effectiveness and specificity of the anti-ET antibody were confirmed by its capacity to prevent renal deterioration caused by a single bolus dose (150 pmol) of synthetic ET, but not by infusion of angiotensin II, norepinephrine, or the thromboxane $A_2$ mimetic U-46619 in isolated kidneys (Perico N, et al., "Endothelin Mediates the Renal Vasoconstriction Induced by Cyclosporine in the Rat," *J Am Soc Nephrol* 1990;1:76).

Others have reported inhibition of ET-1 or ET-2-induced vasoconstriction in rat isolated thoracic aorta using a monoclonal antibody to ET-1 (Koshi T, et al., "Inhibition of Endothelin (ET)-1 and ET-2-Induced Vasoconstriction by Anti-ET-1 Monoclonal Antibody," *Chem Pharm Bull* 1991;39:1295).

Combined administration of ET-1 and ET-1 antibody to rabbits showed significant inhibition of the blood pressure and renal blood flow responses (Miyamori I, et al., Systemic and Regional Effects of Endothelin in Rabbits: Effects of Endothelin Antibody," *Clin Exp. Pharmacol. Physiol* 1990;17:691).

Other investigators have reported that infusion of ET-specific antibodies into spontaneously hypertensive rats (SHR) decreased mean arterial pressure (MAP), and increased glomerular filtration rate and renal blood flow. In the control study with normotensive Wistar-Kyoto rats (WKY), there were no significant changes in these parameters (Ohno A, "Effects of Endothelin-Specific Antibodies and Endothelin in Spontaneously Hypertensive Rats," *J Tokyo Women's Med Coll* 1991;61:951).

In addition, elevated levels of endothelin have been reported in several disease states (see Table I below).

TABLE 1

Plasma Concentrations of ET-1 in Humans

| Condition Reported | Normal Condition | ET Plasma Levels (pg/mL) |
|---|---|---|
| Atherosclerosis | 1.4 | 3.1 pmol/L |
| Surgical operation | 1.5 | 7.3 |
| Buerger's disease | 1.6 | 4.8 |
| Takayasu's arteries | 1.6 | 5.3 |
| Cardiogenic shock | 0.3 | 3.7 |
| Congestive heart failure (CHF) | 9.7 | 20.4 |
| Mild CHF | 7.1 | 11.1 |
| Severe CHF | 7.1 | 13.8 |
| Dilated Cardiomyopathy | 1.6 | 7.1 |
| Preeclampsia | 10.4 pmol/L | 22.6 pmol/L |
| Pulmonary hypertension | 1.45 | 3.5 |
| Acute myocardial infarction | 1.5 | 3.3 |
| (several reports) | 6.0 | 11.0 |
| | 0.76 | 4.95 |
| | 0.50 | 3.8 |
| Subarachnoid hemorrhage | 0.4 | 2.2 |
| Crohn's disease | 0–24 Fmol/mg | 4–64 Fmol/mg |

TABLE 1-continued

Plasma Concentrations of ET-1 in Humans

| Condition Reported | Normal Condition | ET Plasma Levels (pg/mL) |
|---|---|---|
| Ulcerative colitis | 0–24 Fmol/mg | 20–50 Fmol/mg |
| Cold pressor test | 1.2 | 8.4 |
| Raynaud's phenomenon | 1.7 | 5.3 |
| Raynaud's/hand cooling | 2.8 | 5.0 |
| Hemodialysis | <7 | 10.9 |
| (several reports) | 1.88 | 4.59 |
| Chronic renal failure | 1.88 | 10.1 |
| Acute renal failure | 1.5 | 10.4 |
| Uremia before hemodialysis | 0.96 | 1.49 |
| Uremia after hemodialysis | 0.96 | 2.19 |
| Essential hypertension | 18.5 | 33.9 |
| Sepsis syndrome | 6.1 | 19.9 |
| Postoperative cardiac | 6.1 | 11.9 |
| Inflammatory arthritides | 1.5 | 4.2 |
| Malignant hemangioendothelioma | 4.3 | 16.2 (after removal) |

Burnett and co-workers recently demonstrated that exogenous infusion of ET (2.5 ng/kg/mL) to anesthetized dogs, producing a doubling of the circulating concentration, did have biological actions (Lerman A, et al., "Endothelin Has Biological Actions at Pathophysiological Concentrations," *Circulation* 1991;83:1808). Thus heart rate and cardiac output decreased in association with increased renal and systemic vascular resistances and antinatriuresis. These studies support a role for endothelin in the regulation of cardiovascular, renal, and endocrine function.

In the anesthetized dog with congestive heart failure, a significant two- to threefold elevation of circulating ET levels has been reported (Cavero PG, et al., "Endothelin in Experimental Congestive Heart Failure in the Anesthetized Dog," *Am J Physiol* 1990;259:F312), and studies in humans have shown similar increases (Rodeheffer RJ, et al., "Circulating Plasma Endothelin Correlates With the Severity of Congestive Heart Failure in Humans," *Am J Hypertension* 1991;4:9A). When ET was chronically infused into male rats, to determine whether a long-term increase in circulating ET levels would cause a sustained elevation in mean arterial blood pressure, significant, sustained, and dose-dependent increases in mean arterial blood pressure were observed. Similar results were observed with ET-3 although larger doses were required (Mortenson LH, et al., "Chronic Hypertension Produced by Infusion of Endothelin in Rats," *Hypertension* 1990;15:729). Recently the nonpeptide endothelin antagonist RO 46-2005 has been reported to be effective in models of acute renal ischemia and subarachnoid hemorrhage in rats (3rd International Conference on Endothelin, Houston, Tex., February 1993). In addition, the $ET_A$ antagonist BQ- 153 has also been shown to prevent early cerebral vasospasm following subarachnoid hemorrhage after intracisternal injection (Clozel M., et al., *Life Sciences* 1993;52:825); to prevent blood pressure increases in stroke-prone spontaneously hypertensive rats (Nishikibe M, et al., *Life Sciences* 1993;52:717); and to attenuate the renal vascular effects of ET-1 in anaesthetized pigs (Cirino M, et al., *J Pharm Pharmacol* 1992;44:782).

Plasma endothelin-1 levels were dramatically increased in a patient with malignant hemangio-endothelioma (Nakagawa K, et al., *Nippon Hifuka Gakkai Zasshi* 1990;100:1453).

The ET receptor antagonist BQ-123 has been shown to block ET-1-induced bronchoconstriction and tracheal smooth muscle contraction in allergic sheep providing evidence for expected efficacy in bronchopulmonary diseases such as asthma (Noguchi, et al., *Am Rev Respir Dis* 1992;145(4 Part 2):A858).

Circulating endothelin levels are elevated in women with preeclampsia and correlate closely with serum uric acid levels and measures of renal dysfunction. These observations indicate a role for ET in renal constriction in preeclampsia (Clark BA, et al., *Am J Obstet Gynecol* 1992;166:962).

Plasma immunoreactive endothelin-1 concentrations are elevated in patients with sepsis and correlate with the degree of illness and depression of cardiac output (Pittett J, et al., *Ann Surg* 1991;213(3):261).

In addition, the ET-1 antagonist BQ-123 has been evaluated in a mouse model of endotoxic shock. This $ET_A$ antagonist significantly increased the survival rate in this model (Toshiaki M, et al., 20.12.90. EP 0 436 189 A1).

Endothelin is a potent agonist in the liver eliciting both sustained vasoconstriction of the hepatic vasculature and a significant increase in hepatic glucose output (Gandhi CB, et al., *J. Biol. Chem.* 1990;265(29):17432). In streptozotocin-diabetic rats, there is an increased sensitivity to endothelin-1 (Tammesild PJ, et al., *Clin Exp Pharmacol Physiol* 1992;19 (4):261). In addition, increased levels of plasma ET-1 have been observed in microalbuminuric insulin-dependent diabetes mellitus patients indicating a role for ET in endocrine disorders such as diabetes (Collier A, et al., *Diabetes Care* 1992;15(8):1038).

$ET_A$ antagonist receptor blockade has been found to produce an antihypertensive effect in normal to low renin models of hypertension with a time course similar to the inhibition of ET-1 pressor responses (Basil MK, et al., *J Hypertension* 1992;10(Suppl 4):S49). The endothelins have been shown to be arrhythmogenic, and to have positive chronotropic and inotropic effects, thus ET receptor blockade would be expected to be useful in arrhythmia and other cardiovascular disorders (Han S-P, et al., *Life Sci* 1990;46:767).

The widespread localization of the endothelins and their receptors in the central nervous system and cerebrovascular circulation has been described (Nikolov RK, et al., *Drugs of Today* 1992;28(5):303). Intracerebroventricular administration of ET-1 in rats has been shown to evoke behavioral effects. These factors strongly suggest a role for the ETs in neurological disorders. The potent vasoconstrictor action of ETs on isolated cerebral arterioles suggests the importance of these peptides in the regulation of cerebrovascular tone. Increased ET levels have been reported in some CNS disorders, i.e., in the CSF of patients with subarachnoid hemorrhage and in the plasma of women with preeclampsia. Stimulation with ET-3 under conditions of hypoglycemia have been shown to accelerate the development of striatal damage as a result of an influx of extracellular calcium. Circulating or locally produced ET has been suggested to contribute to regulation of brain fluid balance through effects on the choroid plexus and CSF production. ET-1-induced lesion development in a new model of local ischemia in the brain has been described.

Circulating and tissue endothelin immunoreactivity is increased more than twofold in patients with advanced atherosclerosis (Lerman A., et al., *New England J Med* 1991;325:997). Increased endothelin immunoreactivity has also been associated with Buerger's disease (Kanno K, et al.,

*J Amer Med Assoc* 1990;264 2868) and Raynaud's phenomenon (Zamora MR, et al., *Lancet* 1990;336:1144). Likewise, increased endothelin concentrations were observed in hypercholesterolemic rats (Horio T, et al., *Atherosclerosis* 1991;89:239).

An increase of circulating endothelin levels was observed in patients that underwent percutaneous transluminal coronary angioplasty (PTCA) (Tahara A, et al., *Metab Clin Exp* 1991;40:1235; Sanjay K, et al., *Circulation* 1991;84(Suppl. 4):726).

Increased plasma levels of endothelin have been measured in rats (Stelzner TJ, et al., *Am J Physiol* 1992;262:L614) and humans (Miyauchi T, et al., *Jpn J Pharmacol* 1992;58:279P; Stewart DJ, et al., *Ann Internal Medicine* 1991;114:464) with pulmonary hypertension.

Elevated levels of endothelin have also been measured in patients suffering form ischemic heart disease (Yasuda M, et al., *Amer Heart J* 1990;119:801; Ray SG, et al., *Br Heart J* 1992;67:383) and either stable or unstable angina (Stewart JT, et al., *Br Heart J* 1991;66:7).

Infusion of an endothelin antibody 1 hour prior to and 1 hour after a 60-minute period of renal ischemia resulting in changes in renal function versus control. In addition, an increase in glomerular platelet-activating factor was attributed to endothelin (Lopez-Farre A, et al., *J Physiology* 1991;444:513-). In patients with chronic renal failure as well as in patients on regular hemodialysis treatment mean plasma endothelin levels were significantly increased (Stockenhuber F, et al., *Clin Sci* (Lond.) 1992;82:255). In addition, it has been suggested that the proliferative effect of endothelin on mesangial cells may be a contributing factor in chronic renal failure (Schultz PJ, *J Lab Clin Med* 1992;119:448).

Also, Haleen, S., et al., *FASEB J.* April 1994, demonstrated efficacy of an $ET_A/ET_B$ antagonist, PD 145065, which essentially also blocks all ET function (similar to an ECE inhibitor) in a severe model of acute renal failure.

The effects of endothelin receptor blockade on ischemia-induced acute renal failure and mortality were assessed in rats undergoing unilateral nephrectomy and global ischemia in the remaining kidney. Sprague Dawley male rats (300–400 g) were housed in metabolic cages for 2 days before and 7 days after renal injury; urine output and plasma creatinine levels were monitored daily. On the day of renal injury, rats were anesthetized with sodium pentobarbital (50 mg/kg, IP), heparinized (50 units, IV), and instrumented with a tail vein canulae for drug or vehicle infusion. Both kidneys were exposed via a flank incision and the right kidney was removed. The left renal artery was clamped for 60 minutes and released. PD 145065 was infused 60 minutes prior to and following the ischemic period. Renal injury was evident 1 and 2 days following ischemia from a tenfold increase in plasma creatinine levels and significant decreases in urine output. Mortality occurred primarily between the second and third days post-injury. However, mortality was significantly less (52%, N=23) in rats treated with PD 145065 compared to vehicle rats (83%, N-23). In addition, urine output on the second day following renal injury was significantly different between treatment groups on either the first or second days post-injury. Thus blockade of endothelin receptors with PD 145065 significantly decreases mortality in rats subjected to ischemia-induced renal failure.

Local intra-arterial administration of endothelin has been shown to induce small intestinal mucosal damage in rats in a dose-dependent manner (Mirua S, et al., *Digestion* 1991;48:163). Administration of endothelin-1 in the range of 50–500 pmol/kg into the left gastric artery increased the tissue type plasminogen activator release and platelet activating formation and induced gastric mucosal hemorrhagic change in a dose-dependent manner (Kurose I, et al., *Gut* 1992;33:868). Furthermore, it has been shown that an anti-ET-1 antibody reduced ethanol-induced vasoconstriction in a concentration-dependent manner (Masuda E, et al., *Am J Physiol* 1992;262:G785). Elevated endothelin levels have been observed in patients suffering from Crohn's disease and ulcerative colitis (Murch SR, et al., *Lancet* 1992;339:381).

Additionally, there is a correlation between the inhibition of ECE in an in vitro assay, as used and described for the quinazolines of the present invention, and demonstration of in vivo activity in various pathophysiological conditions. For example, Grover, G. J., et al., *J. Pharmacol. Exp. Ther.* 1992, 263, 1074–1082, tested the effect of phosphoramidon, an ECE inhibitor, in a rat model of ischemia. Thus, Grover, G. J., et al. determined the effect of endothelin-1 (ET-1) and big ET-1 on coronary flow and contractile function in isolated nonischemic and ischemic rat hearts. Both ET-1 ($IC_{50}$=12 pMol) and big ET-1 ($IC_{50}$=2 nMol) reduced coronary flow in a concentration-dependent manner. Both 30 pMol ET-1 and 10 nMol big ET-1 pretreatment significantly reduced the time to contracture in globally ischemic rat hearts, suggesting a proischemic effect. Phosphoramidon ($IC_{50}$=100 µM) and BQ-123 (0.3 µM, $ET_A$ receptor antagonist) abolished the preischemic increase in coronary perfusion pressure induced by big ET-1 as well as its proischemic effect. Phosphoramidon was also given IV to rats subjected to coronary occlusion and reperfusion and was found to significantly reduce infarct size 24 hour postischemia. Phosphoramidon has been disclosed to be an effective inhibitor of ECE, $IC_{50}$=1 µM. (European Published Patent Application EP 0518299 A2 and International Published Patent Application WO 92/13944).

Depending on the nature of substituent(s) attached, quinazolines have been described, for example, as fungicides, insecticides, bronchodilators, hypotensive agents, analgesics and active against the trachoma virus. See, e.g., German Patents 1,800,709, 4,208,254, U.K. Patent Specification 1,199,768, U.S. Pat. Nos. 3,184,462, 3,340, 260, U.K. Patent 857,362, Patterson, S. E., et al., *J. Heterocycl. Chem.* (1992), 29(4), 703–6, Brown, D. J., et al., *Aust. J. Chem.* (1985), 38(3), 467–74, Genther, C. S., et al., *J. Med. Chem.* (1977), 20(2), 237–43, and Russian Patent SU-466,233. Also, European Patent Publication No. 0579496A1 describes 4-aminoquinazolines having inhibitory effect on cGMP-PDE, or additionally on $TXA_2$ synthetase. The inhibition of cGMP-PDE is considered to be useful in diseases induced by enhancement of the metabolism of cGMP, such as hypertension, heart failure, myocardial infarction, angina, atherosclerosis, cardiac edema, pulmonary hypertension, renal insufficiency, nephrotic edema, hepatis edema, asthma, bronchitis, dementia, and immunodeficiency. The inhibition of thromboxane $A_2$ ($TXA_2$) synthetase is said to be useful for inflammation, hypertension, thrombosis, arteriosclerosis, cerebral apoplexy, asthma, myocardial infarction, cardiostenosis and cerebral infarction.

It has now been discovered that certain known and novel quinazoline derivatives possess a new property not previously reported for this class of compounds, which are inhibitors of endothelin converting enzyme. The quinazoline compounds of the present invention are thus useful in treating diseases associated with elevated levels of endothelin as mentioned above.

SUMMARY OF THE INVENTION

Accordingly, the present invention is a compound of Formula I

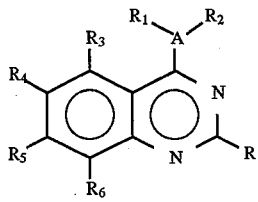

wherein A is N, CH or $S(O)_n$ where n is 0, 1 or 2;

R is lower alkyl,
halo-lower alkyl,
aryl,
aryl-lower alkyl,
heteroaryl, or
heteroaryl-lower alkyl;

$R_1$ is hydroxyalkyl containing at least 2 carbon atoms when A is N or S,
lower alkoxyalkyl,
thioalkyl containing at least 2 carbon atoms when A is N or S,
lower alkyl thioalkyl,
carboxyalkyl,
an $R_7$–$R_8$ -aminoalkyl group in which $R_7$ and $R_8$ are each independently hydrogen, or lower alkyl or when taken together with amino form a 5–7 membered saturated heterocyclic ring optionally interrupted by a second heteroatom selected from nitrogen, oxygen and sulfur, and where the heteroatom is nitrogen, said nitrogen atom may be substituted by alkyl, carboxyalkyl, or lower alkyl carboxyalkyl, and wherein said ring may be further substituted at a carbon atom by
alkyl,
amino,
aminoalkyl,
monoalkylaminoalkyl,
dialkylaminoalkyl,
carboxy,
carboxyalkyl,
alkylcarboxyalkyl,
thio,
thioalkyl,
alkylthioalkyl,
hydroxy,
hydroxyalkyl,
alkoxy, or
alkoxyalkyl,
wherein the alkyl portion of the $R_1$ groups defined above my be further substituted on the alkyl chain by
aminoalkyl,
monoalkylaminoalkyl,
dialkylaminoalkyl,
carboxyalkyl,
alkyl carboxyalkyl,
thioalkyl,
alkylthioalkyl,
hydroxyalkyl, or
alkoxyalkyl,
a 5–7 membered saturated or monounsaturated carbocyclic ring optionally fused to a benzene ring, or a 5,6 or 6,6-membered bicyclic carbocyclic rings, said rings attached directly to A or through an alkyl group, or a 5–7 membered saturated heterocyclic ring optionally fused to a benzene ring, or 5,6 or 6,6-membered heterocyclic bicyclic rings, having at least 1 heteroatom, wherein said ring is attached directly to A or through an alkyl group linking A with the ring at a carbon atom, said rings being optionally substituted by
alkyl,
amino,
aminoalkyl,
monoalkylaminoalkyl,
dialkylaminoalkyl,
carboxy,
carboxyalkyl,
alkylcarboxyalkyl,
thio,
thioalkyl,
alkylthioalkyl,
hydroxy,
hydroxyalkyl,
alkoxy, or
alkoxyalkyl,
$OR_9$ wherein $R_9$ is hydrogen or lower alkyl,
$NR_9R_{10}$ wherein $R_9$ and $R_{10}$ are each independently hydrogen, or lower alkyl,
$CO_2R_9$ wherein $R_9$ is as defined above,
when A is N, a carboxy-lower alkyl side chain of a natural or unnatural α-aminoacid, or
when A is S and n is zero, a hydrogen atom;

$R_2$ is absent when A is S, a hydrogen atom or lower alkyl and, when A is N, $R_1$ and $R_2$ may be combined together to form a 5- or 6-membered saturated ring optionally containing an additional nitrogen atom in the ring at the 3- or 4- position, and the additional nitrogen atom may optionally be substituted by alkyl, carboxyalkyl or lower alkyl carboxyalkyl, and the ring may be further substituted at a carbon atom by
alkyl,
amino,
aminoalkyl,
monoalkylaminoalkyl,
dialkylaminoalkyl,
carboxy,
carboxyalkyl,
alkylcarboxyalkyl,
thio,
thioalkyl,
alkylthioalkyl,
hydroxy,
hydroxyalkyl,
alkoxy, or
alkoxyalkyl;

$R_3$, $R_4$, $R_5$ and $R_6$ are each independently hydrogen, halo, lower alkyl, cycloalkyl, halo-lower alkyl, lower alkoxy, hydroxyalkyl, aminoalkyl, lower alkyl aminoalkyl, di-lower alkyl aminoalkyl, nitro, cyano, $SO_2NR_{11}R_{12}$, $SO_2R_9$, $CO_2R_9$, $CONR_{11}R_{12}$, $NR_{11}R_{12}$ in which $R_{11}$ and $R_{12}$ are each independently hydrogen, lower alkyl, aryl, heteroaryl or aralkyl, or two of adjacent members $R_3$ to $R_6$ may be combined together to form a methylenedioxy group, and ethylenedioxy group or a benzene ring, or a pharmaceutically acceptable acid addition or base salt thereof; with the following provisos:

(a) when A is N, and $R_1$ is aminoalkyl, lower alkyl aminoalkyl, di-lower alkyl aminoalkyl, or hydroxyalkyl, then $R_4$ is iodo or $R_5$ is halo and R is halo-lower alkyl;

(b) when A is N and $R_1$ is a pyrrolidine optionally substituted by alkyl or carboxy-lower alkyl and $R_3$ and $R_6$ are as defined above, then R is halo-lower alkyl, aryl, aryl-lower alkyl, heteroaryl, or heteroaryl-lower alkyl, and (c) when A is N, $R_3$ and $R_6$ are as defined above and $R_1$ and $R_2$ with A form a piperazine ring, then R is aryl, aryl-lower alkyl, heteroaryl or heteroaryl-lower alkyl, or when, in addition, $R_4$ is halo, R can be halo-lower alkyl.

Since elevated levels of endothelin have been shown to be involved in a number of pathophysiological states, a second aspect of the present invention is a method of treating diseases associated with elevated levels of endothelin comprising administering to a host suffering therefrom a therapeutic effective amount of an inhibitor of endothelin converting enzyme of the Formula I

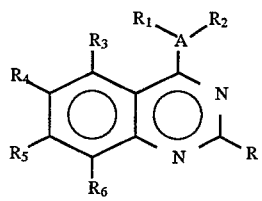

wherein A is N, CH or $S(O)_n$ where n is 0, 1 or 2;

R is lower alkyl, halo-lower alkyl, aryl, aryl-lower alkyl, heteroaryl, or heteroraryl-lower alkyl;

$R_1$ is hydroxyalkyl containing at least 2 carbon atoms when A is N or S, lower alkoxyalkyl, thioalkyl containing at least 2 carbon atoms when A is N or S, lower alkyl thioalkyl, carboxyalkyl, an $R_7$-$R_8$-aminoalkyl group in which $R_7$ and $R_8$ are each independently hydrogen, or lower alkyl or when taken together with amino form a 5–7 membered saturated heterocyclic ring optionally interrupted by a second heteroatom selected from nitrogen, oxygen and sulfur, and where the heteroatom is nitrogen, said nitrogen atom may be substituted by alkyl, carboxyalkyl, or lower alkyl carboxyalkyl, and wherein said ring may be further substituted at a carbon atom by alkyl, amino, aminoalkyl, monoalkylaminoalkyl, dialkylaminoalkyl, carboxy, carboxyalkyl, alkylcarboxyalkyl, thio, thioalkyl, alkylthioalkyl, hydroxy, hydroxyalkyl, alkoxy, or alkoxyalkyl, wherein the alkyl portion of the $R_1$ groups defined above may be further substituted on the alkyl chain by aminoalkyl, monoalkylaminoalkyl, dialkylaminoalkyl, carboxyalkyl, alkylcarboxyalkyl, thioalkyl, alkylthioalkyl, hydroxyalkyl, or alkoxyalkyl, a 5–7 membered saturated or monounsaturated carbocyclic ring optionally fused to a benzene ring, or a 5,6 or 6,6-membered bicyclic carbocyclic rings, said rings attached directly to A or through an alkyl group, or a 5–7 membered saturated heterocyclic ring optionally fused to a benzene ring, or 5,6 or 6,6-membered heterocyclic bicyclic rings, having at least 1 heteroatom, wherein said ring is attached directly to A or through an alkyl group linking A with the ring at a carbon atom, said rings being optionally substituted by alkyl, amino, aminoalkyl, monoalkylaminoalkyl, dialkylaminoalkyl, carboxy, carboxyalkyl, alkylcarboxyalkyl, thio, thioalkyl, alkylthioalkyl, hydroxy, hydroxyalkyl, alkoxy, or alkoxyalkyl, $OR_9$ wherein $R_9$ is hydrogen or lower alkyl, $NR_9R_{10}$ wherein $R_9$ and $R_{10}$ are each independently hydrogen, or lower alkyl, $CO_2R_9$ wherein $R_9$ is as defined above, when A is N, a carboxy-lower alkyl side chain of a natural or unnatural α-aminoacid, or when A is S and n is zero, a hydrogen atom;

$R_2$ is absent when A is S, a hydrogen atom or lower alkyl and, when A is N, $R_1$ and $R_2$ may be combined together to form a 5- or 6-membered saturated ring optionally containing an additional nitrogen atom in the ring at the 3- or 4-position, and the additional nitrogen atom may optionally be substituted by alkyl, carboxyalkyl or lower alkyl carboxyalkyl, and the ring may be further substituted at a carbon atom by alkyl, amino, aminoalkyl, monoalkylaminoalkyl, dialkylaminoalkyl, carboxy, carboxyalkyl, alkylcarboxyalkyl, thio, thioalkyl, alkylthioalkyl, hydroxy, hydroxyalkyl, alkoxy, or alkoxyalkyl;

$R_3$, $R_4$, $R_5$ and $R_6$ are each independently hydrogen, halo, lower alkyl, cycloalkyl, halo-lower alkyl, lower alkoxy, hydroxyalkyl, aminoalkyl, lower alkyl aminoalkyl, di-lower alkyl aminoalkyl, nitro, cyano, $SO_2NR_{11}R_{12}$, $SO_2R_9$, $CO_2R_9$, $CONR_{11}R_{12}$, $NR_{11}R_{12}$ in which $R_{11}$ and $R_{12}$ are each independently hydrogen, lower alkyl, aryl, heteroaryl or aralkyl, or two of adjacent members $R_3$ to $R_6$ may be combined together to form a methylenedioxy group, and ethylenedioxy group or a benzene ring, or a pharmaceutically acceptable acid addition or base salt thereof Such diseases include acute and chronic renal failure, hypertension, myocardial infarction and myocardial ischemia, cerebral vasospasm, cirrhosis, septic shock, congestive heart failure, endotoxic shock, subarachnoid hemorrhage, arrhythmias, asthma, preeclampsia, atherosclerotic disorders including Raynaud's disease and restenosis, angina, cancer, pulmonary hypertension, ischemic disease, gastric mucosal damage, hemorrhagic shock, ischemic bowel disease, diabetes, cerebral ischemia or cerebral infarction resulting from a range of conditions such as thromboembolic or hemorrhagic stroke, cerebral vasospasm, head injury, hypoglycemia, cardiac arrest, status epilepticus, perinatal asphyxia, anoxia such as from drowning, pulmonary surgery, and cerebral trauma.

A third aspect of the present invention is a pharmaceutical composition for administering an effective amount of a compound of Formula I in admixture with a pharmaceutically acceptable carrier in the treatment methods mentioned above in unit dosage form.

DETAILED DESCRIPTION OF THE INVENTION

In the compounds of the present invention, the term "alkyl", in general and unless specifically limited, means a straight or branched hydrocarbon radical having from 1 to 12 carbon atoms and includes, for example, methyl, ethyl, n-propyl, isopropyl, n-butyl, sec-butyl, isobutyl, tert-butyl, n-pentyl, n-hexyl, n-heptyl, n-octyl, n-nonyl, n-decyl, undecyl, dodecyl, and the like. The term "alkyl" also has the same meaning when used as a suffix for "aminoalkyl", "hydroxyalkyl", "thioalkyl", "carboxyalkyl" and the like.

The term "lower" preceding "alkyl" includes only those straight or branched hydrocarbon radicals defined above having from 1 to 7 carbon atoms.

The term "alkoxy" is O-alkyl as defined above for alkyl or lower alkyl.

The term "aryl" means an aromatic radical which is a phenyl group, a naphthyl group, a biphenyl group, a pyrenyl group, an anthracenyl group, 3,3-diphenylalanyl, 10,11-dihydro-5H-dibenzo-[a,d]-(cyclohepten-5-yl)glycyl, or a fluorenyl group and the like, unsubstituted or substituted by 1 to 4 substituents selected from lower alkyl as defined above, lower alkoxy as defined above, trifluoromethyl, nitro, halogen, CN, $SO_3H$, $SO_2NH_2$, $SO_2CH_3$, COOH, COO-lower alkyl, $CONH_2$, CO-lower alkyl, $NH_2$, NH-lower alkyl,N,N-di-lower alkyl, NH-aralkyl, N-di-aralkyl,N,N-lower alkyl-aralkyl, in which aralkyl is as defined below.

The term "arylalkyl" or "aralkyl" means an aromatic radical attached to an alkyl radical wherein aryl and alkyl are as defined above, for example, benzyl, fluorenylmethyl, and the like.

The term "heteroaryl" means a heteroaromatic radical which includes 2- or 3-thienyl, 2- or 3-furanyl, 2- or 3-pyrrolyl, 2-, 4-, or 5-imidazolyl, 3-, 4-, or 5-pyrazolyl, 2-, 4-, or 5-thiazolyl, 3-, 4-, or 5-isothiazolyl, 2-, 4-, or 5-oxazolyl, 3-, 4-, or 5-isoxazolyl, 3- or 5-1,2,4-triazolyl, 4- or 5-1,2,3-triazolyl, tetrazolyl, 2-, 3-, or 4-pyridinyl, 3-, 4-, or 5-pyridazinyl, 2-pyrazinyl, 2-, 4-, or 5-pyrimidinyl, 2-, 3-, 4-, 5-, 6-, 7-, or 8-quinolinyl, 1-, 3-, 4-, 5-, 6-, 7-, or 8-isoquinolinyl, 2 -, 3 -, 4 -, 5-, 6-, or 7- indolyl, N-formyl-2-, 3-, 4-, 5-, 6-, 7-indolyl, 2-, 3-, 4-, 5-, 6-, 7-benzo[b]thienyl, or 2-, 4-, 5-, 6-, or 7-benzoxazolyl, 2-, 4-, 5-, 6-, or 7-benzimidazolyl, 2-, 4-, 5-, 6-, 7-benzothiazolyl, unsubstituted or substituted by 1 to 2 substituents selected from those defined above for aryl.

"Halogen" or "halo" is fluorine, chlorine, bromine, or iodine.

A "5–7 membered saturated heterocyclic ring optionally interrupted by a second heteroatom selected from nitrogen, oxygen and sulfur" includes, for example, pyrrolidine, pyrrazolidine, imidazolidine, oxazolidine, thiaoxazolidine, piperidine, piperazine, morpholine, thiamorpholine, homopiperidine, and the like. When the second nitrogen atom is nitrogen as, for example, an imidazolidine or piperazine, said second nitrogen atom my be substituted by alkyl, carboxyalkyl or lower alkyl-carboxyalkyl. The carbon atoms of the above 5–7 membered heterocyclic ring may be substituted independently by alkyl, amino, aminoalkyl, monoalkylaminoalkyl, dialkylaminoalkyl, carboxy, carboxyalkyl, alkylcarboxyalkyl, thio, thioalkyl, alkylthioalkyl, hydroxy, hydroxyalkyl, alkoxy or alkoxyalkyl.

For purposes of the present invention, the above definition applies to the compounds of Formula I where $R_1$ is $R_7R_8$ aminoalkyl and where $R_7$ and $R_8$ are taken together with the nitrogen atom. Said nitrogen atom is linked to "A" in Formula I.

A "5–7 membered saturated or monounsaturated carbocyclic ring optionally fused to a benzene ring" includes, for example, cyclopentane, cyclopentene, cyclohexane, cyclohexene, cycloheptane, cycloheptene, indane, tetralin and benzosuberane.

"5,6 or 6,6-Membered bicyclic carbocyclic rings" include, for example, bicyclo[3.2.1]octane or bicyclo [2.2.2] octane.

A "5–7 membered saturated heterocyclic ring optionally fused to a benzene ring" includes, for example, the "5–7 membered saturated heterocyclic ring optionally interrupted by a second heteroatom selected from nitrogen, oxygen and sulfur" as defined above and, in addition, dihydrobenzofuran, dihydroisobenzofuran, dihydrobenzothiophene, dihydroisobenzothiophene, indoline, isoindoline, chroman, isochroman, thiochroman, isothiochroman, tetrahydroquinoline, tetrahydroisoquinoline, and the like.

"5,6 or 6,6-Membered heterocyclic bicyclic rings" include, for example, 1-aza-bicyclo[3,2,1]octane or 1-aza-bicyclo[2.2.2]octane.

The above-defined carbocyclic and heterocyclic rings come under the definition of $R_1$ in the compounds of Formula I and, as such, are radicals where a carbon atom of said ring is attached directly to "A" of Formula I or through an alkyl chain linking the ring at a carbon atom with "A".

The above-defined carbocyclic and heterocyclic rings may optionally be substituted at a ring carbon atom by alkyl, amino, aminoalkyl, monoalkylaminoalkyl, dialkylaminoalkyl, carboxy, carboxyalkyl, alkylcarboxyalkyl, thio, thioalkyl, alkylthioalkyl, hydroxy, hydroxyalkyl, alkoxy, or alkoxyalkyl.

The following table provides a representative list of natural and modified or unsaturated amino acids with abbreviations used in the present invention.

| Abbreviation* | Amino Acid |
|---|---|
| Ala | Alanine |
| Arg | Arginine |
| Asn | Asparagine |
| Asp | Aspartic acid |
| Cys | Cysteine |
| Glu | Glutamic acid |
| Gln | Glutamine |
| Gly | Glycine |
| His | Histidine |
| Ile | Isoleucine |
| Leu | Leucine |
| Lys | Lysine |
| Met | Methionine |
| Phe | Phenylalanine |
| Pro | Proline |
| Ser | Serine |
| Thr | Threonine |
| Trp | Tryptophan |
| Tyr | Tyrosine |
| Val | Valine |
| Nva | Norvaline |
| Nle | Norleucine |
| Alg | 2-Amino-4-pentanoic acid (allylgycine) |
| Cpn | 2-Amino-3-cyclopropane propanoic acid (Cyclopropylalanine) |
| Chx | Cyclohexylalanine (Hexahydrophenylalanine) |
| His (Dnp) | $N^{im}$-2,4-Dinitrophenyl-histidine |
| HomoPhe | 2-Amino-5-phenylpentanoic acid (homophenylalanine) |
| 1-Nal | 3-(1'-Naphthyl)alanine |
| 2-Nal | 3-(2'-Naphthyl)alanine |
| Pgy | 2-Aminopentanoic acid (Propylglycine) |
| Pyr | 2-Amino-3-(3-pyridyl)-propanoic acid (3-Pyridylalanine) |
| Tza | 2-Amino-3-(4-thiazolyl)-propanoic acid |
| Tyr (Ot-Bu) | O-Tertiary butyltyrosine |
| Tyr (OMe) | O-methyltyrosine |
| Tyr (OEt) | O-ethyltyrosine |
| Trp (For) | $N^{in}$-Formyltryptophan |
| His (t-Bu) | $N^{im}$-tertiary butylhistidine |
| His (Cφ₃) | $N^{im}$-triphenylmethyl-histidine ($N^{im}$-tritylhistidine) |
| Trp (Me) | $N^{in}$-Methyltryptophan |
| Asp (Ot-Bu) | Aspartaic acid 4-tertiary butyl ester |
| Asp (OMe) | Aspartic acid 4-methyl ester |
| Asp (OBn) | Aspartic acid 4-benzyl ester |
| Glu (Ot-Bu) | Glutamic acid 5-tertiary butyl ester |
| Glu (Ome) | Glutamic acid 5-methyl ester |
| Bta | 3-Benzothienyl alanine |
| Bfa | 3-Benzofuranyl alanine |

*If the optical activity of the amino acid is other than L (S), the amino acid or abbreviation is preceded by the appropriate configuration D (R) or DL (RS).

The compounds of Formula I are capable of further forming both pharmaceutically acceptable acid addition and/or base salts. All of these forms are within the scope of the present invention.

Pharmaceutically acceptable acid addition salts of the compounds of Formula I include salts derived from nontoxic inorganic acids such as hydrochloric, nitric, phosphoric, sulfuric, hydrobromic, hydriodic, hydrofluoric, phosphorous, and the like, as well as the salts derived from nontoxic organic acids, such as aliphatic mono- and dicarboxylic acids, phenyl-substituted alkanoic acids, hydroxy alkanoic acids, alkanedioic acids, aromatic acids, aliphatic and aromatic sulfonic acids, etc. Such salts thus include sulfate, pyrosulfate, bisulfate, sulfite, bisulfite, nitrate, phosphate, monohydrogenphosphate, dihydrogenphosphate, metaphosphate, pyrophosphate, chloride, bromide, iodide, acetate, trifluoroacetate, propionate, caprylate, isobutyrate, oxalate, malonate, succinate, suberate, sebacate, fumarate, maleate, mandelate, benzoate, chlorobenzoate, methylbenzoate, dinitrobenzoate, phthalate, benzenesulfonate, toluenesulfonate, phenylacetate, citrate, lactate, maleate, tartrate, methanesulfonate, and the like. Also contemplated are salts of amino acids such as arginate and the like and gluconate, galacturonate (see, for example, Berge SM, et al., "Pharmaceutical Salts," J of Pharma Sci 1977;66:1.

The acid addition salts of said basic compounds are prepared by contacting the free base form with a sufficient amount of the desired acid to produce the salt in the conventional manner. Preferably, a compound of Formula I can be converted to an acidic salt by treating with an aqueous solution of the desired acid, such that the resulting pH is less than 4. The free base form may be regenerated by contacting the salt form with a base and isolating the free base in the conventional manner. The free base forms differ from their respective salt forms somewhat in certain physical properties such as solubility in polar solvents, but otherwise the salts are equivalent to their respective free base for purposes of the present invention.

Pharmaceutically acceptable base addition salts are formed with metals or amines, such as alkali and alkaline earth metals or organic amines. Examples of metals used as cations are sodium, potassium, magnesium, calcium, and the like. Examples of suitable amines are N,N'-dibenzylethylenediamine, chloroprocaine, choline, diethanolamine, dicyclohexylamine, ethylenediamine, N-methylglucamine, and procaine (see, for example, Berge SM, et al., "Pharmaceutical Salts," J of Pharma Sci, 1977;66:1.

The base addition salts of said acidic compounds are prepared by contacting the free acid form with a sufficient amount of the desired base to produce the salt in the conventional manner. Preferably, a compound of Formula I can be converted to a base salt by treating with an aqueous solution of the desired base, such that the resulting pH is greater than 9. The free acid form my be regenerated by contacting the salt form with an acid and isolating the free acid in the conventional manner. The free acid forms differ from their respective salt forms somewhat an certain physical properties such as solubility in polar solvents, but otherwise the salts are equivalent to their respective free acid for purposes of the present invention.

Certain of the compounds of the present invention can exist in unsolvated forms as well as solvated forms, including hydrated forms. In general, the solvated forms, including hydrated forms, are equivalent to unsolvated forms and are intended to be encompassed within the scope of the present invention.

Certain of the compounds of the present invention possess one or more chiral centers and each center may exist in the R(D) or S(L) configuration. The present invention includes all enantiomeric and epimeric forms as well as the appropriate mixtures thereof.

Of the above compounds of Formula I, preferred are those:

(1) wherein A is N;

(2) wherein $R_1$ is aminoalkyl, lower alkyl aminoalkyl, di-lower alkylaminoalkyl, hydroxyalkyl or thioalkyl, and R is halo-lower alkyl, and (3) wherein $R_4$ is iodo and/or $R_5$ is halo.

Other preferred compounds are compounds of Formula II

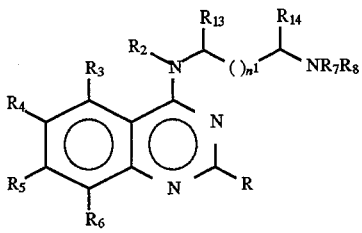

wherein $R_{13}$ and $R_{14}$ are each independently hydrogen, alkyl, aminoalkyl, monoalkylaminoalkyl, dialkylaminoalkyl, carboxyalkyl, alkylcarboxyalkyl, thioalkyl, alkylthioalkyl, hydroxyalkyl, or alkoxyalkyl;

$n^1$ is 0, 1, 2, or 3, and

R, $R_2$, $R_3$, $R_4$, $R_5$, $R_6$, $R_7$ and $R_8$ are as defined above, with the proviso that when $R_7$ and $R_8$ are each independently hydrogen or lower alkyl and $R_3$ and $R_6$ are hydrogen, then $R_4$ is iodo or $R_5$ is halo and R is halo-lower alkyl.

Particularly valuable compounds of the Formula I are, for example, N-(6-iodo-2-trichloromethyl-quinazolin-4-yl)-ethane-1,2-diamine, N-(6-iodo-2-trichloromethyl-quinazolin-4-yl)-N-methyl-ethane-1,2-diamine, N-(6-iodo-2-trichloromethyl-quinazolin-4-yl)-N',N'-dimethyl-ethane-1,2-diamine, N-(7-chloro-2-trichloromethyl-quinazolin-4-yl)-N',N'-diisopropyl-ethane-1,2-diamine, (6-iodo-2-trichloromethyl-quinazolin- 4-yl)-(2-piperidin-1-yl-ethyl)-amine, (6-iodo-2-trichloromethyl-quinazolin-4-yl)-(2-morpholin-4-yl-ethyl)-amine, and N'-(6-iodo-2-trichloromethyl-quinazolin-4-yl)-N,N,N'',N''-tetramethyl-propane-1,2,3-triamine.

Another preferred aspect of the present invention is a compound of Formula III

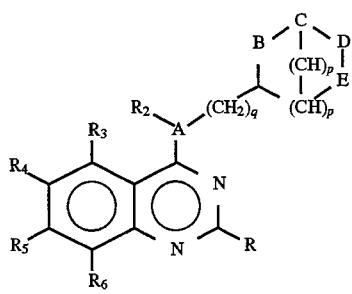

wherein A is N, CH or $S(O)_n$ where n is 0, 1 or 2; and q is 0, 1 or 2;

(a) B, C, D and E are $CH_2$ or $NR_{13}$ in which only one of B, C, D or E is $NR_{13}$ wherein $R_{13}$ is hydrogen, lower alkyl, aralkyl, —$(CH_2)_mCO_2R_9$ in which $R_9$ is hydrogen or lower alkyl, or —$(CH_2)_mNR_9R_{10}$ in which $R_9$ and $R_{10}$ are each independently hydrogen or lower alkyl and m is an integer of 0 to 6, p is an integer from 0 to 2, and r is an integer from 0 to 2, or (b) A is N, C, D and E are absent, p is 0 and B is $NR_{13}$ or —$CH_2NR_{13}$ and attached to $R_2$ to form a 5- or 6-membered ring, in which $R_{13}$ is as defined above;

R is lower alkyl, halo-lower alkyl, phenyl or phenyl substituted by lower alkyl, lower alkoxy, trifluoromethyl, halo, $NO_2$, CN, $SO_3H$, $SO_2NH_2$, $SO_2CH_3$, $COOR_9$ in which $R_9$ is hydrogen or lower alkyl, $CONR_9R_{10}$ wherein $R_9$ and $R_{10}$ are each independently hydrogen or lower alkyl, or $NR_{11}R_{12}$ wherein $R_{11}$ and $R_{12}$ are each independently hydrogen, lower alkyl, aryl, heteroaryl or aralkyl, or heteroaryl;

$R_2$ is absent when A is S, a hydrogen atom or lower alkyl;

$R_3$ and $R_6$ are each independently hydrogen, lower alkyl or lower alkoxy, and $R_4$ and $R_5$ are each independently hydrogen, lower alkyl, lower alkoxy, trifluoromethyl, halo, $NO_2$, CN, $SO_3H$, $SO_2NH_2$, $SO_2CH_3$, $COOR_9$ in which $R_9$ is hydrogen or lower alkyl, $CONR_9R_{10}$ wherein $R_9$ and $R_{10}$ are each independently hydrogen or lower alkyl, or $NR_{11}R_{12}$ wherein $R_{11}$ and $R_{12}$ are each independently hydrogen, lower alkyl, aryl, heteroaryl or aralkyl, or $R_4$ and $R_5$ may be joined together to form a methylenedioxy group or benzene ring, or a pharmaceutically acceptable acid addition or base salt thereof, with the following provisos:

(i) when A is N, and B, C, D and E are defined as in (a) above where p is zero and $R_3$ to $R_6$ are as defined above, then R is halo-lower alkyl, phenyl or substituted phenyl as defined above, or heteroaryl, and (ii) when A is N, $R_3$ to $R_6$ are as defined above and B, C, D and E are defined as in (b) above, R is phenyl or substituted phenyl as defined above or heteroaryl, or, when, in addition, $R_4$ is halo, R can be halo-lower alkyl.

Preferred compounds of Formula III are those:

(1) wherein A is N;

(2) wherein C, D and E are absent; p is 0; B is $NR_{13}$ or —$CH_2NR_{13}$ and attached to $R_2$ to form a 5-or 6-membered ring; R is phenyl or phenyl substituted by lower alkyl, lower alkoxy, trifluoromethyl, halo, $NO_2$, CN, $SO_3H$, $SO_2NH_2$, $SO_2CH_3$, $COOR_9$ in which $R_9$ is hydrogen or lower alkyl, $CONR_9R_{10}$ wherein $R_9$ and $R_{10}$ are each independently hydrogen or lower alkyl, or $NR_{11}R_{12}$ wherein $R_{11}$ and $R_{12}$ are each independently hydrogen, lower alkyl, aryl, heteroaryl or aralkyl; or, alternatively wherein $R_4$ is halo and R is halo-lower alkyl, e.g. 6-iodo-4-(4-methyl-piperazin-1-yl)-2-trichloromethyl-quinazoline or 6-iodo-4-piperazin-1-yl-2-trichloromethyl-quinazoline.

Still another preferred aspect of the present invention is a compound of Formula III, wherein A is N, CH or $S(O)_n$ where n is 0, 1 or 2;

B, C, D, E are $CH_2$ or $NR_{13}$ in which only one of B, C, D, or E is $NR_{13}$ wherein $R_{13}$ is hydrogen, lower alkyl, aralkyl, —$(CH_2)_mCO_2R_9$ in which $R_9$ is hydrogen or lower alkyl, or —$(CH_2)_m$—$NR_9R_{10}$ in which $R_9$ and $R_{10}$ are each independently hydrogen or lower alkyl and m is an integer of 0 to 6, and p is an integer from zero to 2;

R is lower alkyl, halo-lower alkyl, phenyl or phenyl substituted by lower alkyl, lower alkoxy, trifluoromethyl, halo, $NO_2$, CN, $SO_3H$, $SO_2NH_2$, $SO_2CH_3$, $COOR_9$ in which $R_9$ is hydrogen or lower alkyl, $CONR_9R_{10}$ wherein $R_9$ and $R_{10}$ are each independently hydrogen or lower alkyl, or $NR_{11}R_{12}$ wherein $R_{11}$ and $R_{12}$ are each independently hydrogen, lower alkyl, aryl, heteroaryl or aralkyl, or heteroaryl;

$R_2$ is absent when A is S, a hydrogen atom or lower alkyl;

$R_3$ and $R_6$ are each independently hydrogen, lower alkyl or lower alkoxy, and $R_4$ and $R_5$ are each independently hydrogen, lower alkyl, lower alkoxy, trifluoromethyl, halo, $NO_2$, CN, $SO_3H$, $SO_2NH_2$, $SO_2CH_3$, $COOR_9$ in which $R_9$ is hydrogen or lower alkyl, $CONR_9R_{10}$ wherein $R_9$ and $R_{10}$ are each independently hydrogen or lower alkyl, or $NR_{11}R_{12}$ wherein $R_{11}$ and $R_{12}$ are each independently hydrogen, lower alkyl, aryl, heteroaryl or aralkyl, or $R_4$ and $R_5$ may be joined together to form a methylenedioxy group or a benzene ring, or a pharmaceutically acceptable acid addition or base salt thereof, with the proviso that when A is N and p is 0, R is halo-lower alkyl, phenyl or substituted phenyl as defined above, or heteroaryl.

Still another preferred embodiment is a compound of Formula III where A is N, B, D and E are $CH_2$, C is N, p is 1, q is 0 and r is 2, which is (1-aza-bicyclo[2,2,2]oct-3-yl)-(6-iodo-2-trichloromethyl-quinazolin-4-yl)-amine.

A more preferred aspect of the present invention is a compound of Formula IV

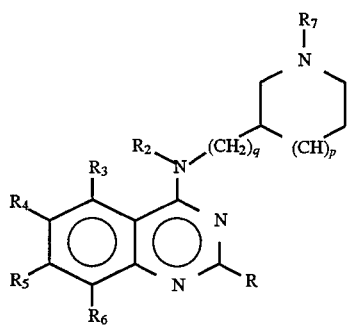

wherein q is 0, 1 or 2 and p is 0 or 1; R is lower alkyl, halo-lower alkyl, phenyl or phenyl substituted by lower alkyl, lower alkoxy, trifluoromethyl, halo, $NO_2$, CN, $SO_3H$, $SO_2NH_2$, $SO_2CH_3$, $COOR_9$ in which $R_9$ is hydrogen or lower alkyl, $CONR_9R_{10}$ wherein $R_9$ and $R_{10}$ are each independently hydrogen or lower alkyl, or $NR_{11}R_{12}$ wherein $R_{11}$ and $R_{12}$ are each independently hydrogen, lower alkyl, aryl, heteroaryl or aralkyl, or heteroaryl;

$R_2$ is a hydrogen atom or lower alkyl;

$R_3$ and $R_6$ are each independently hydrogen, lower alkyl or lower alkoxy, and $R_4$ and $R_5$ are each independently hydrogen, lower alkyl, lower alkoxy, trifluoromethyl, halo, $NO_2$, CN, $SO_3H$, $SO_2NH_2$, $SO_2CH_3$, $COOR_9$ in which $R_9$ is hydrogen or lower alkyl, $CONR_9R_{10}$ wherein $R_9$ and $R_{10}$ are each independently hydrogen or lower alkyl, or $NR_{11}R_{12}$ wherein $R_{11}$ and $R_{12}$ are each independently hydrogen, lower alkyl, aryl, heteroaryl or aralkyl, or $R_4$ and $R_5$ may be joined together to form a methylenedioxy group or a benzene ring;

$R_7$ is hydrogen, lower alkyl, aralkyl, —$(CH_2)_mCO_2R_9$ in which $R_9$ is hydrogen or lower alkyl, or —$(CH_2)_m$—$NR_9R_{10}$ in which $R_9$ and $R_{10}$ are each independently hydrogen or lower alkyl and m is an integer of 1 to 6, or a pharmaceutically acceptable acid addition or base salt thereof; with the proviso that when p is 0, q is 1 or 2.

More preferred of the compounds of Formula IV are those wherein $R_4$ and $R_5$ are each independently hydrogen, trifluoromethyl, halo, $NO_2$, CN, $SO_3H$, $SO_2NH_2$, $SO_2CH_3$, $COOR_9$ in which $R_9$ is hydrogen or lower alkyl, or $CONR_9R_{10}$ wherein $R_9$ and $R_{10}$ are each independently hydrogen or lower alkyl, and R is lower alkyl, halo-lower alkyl, phenyl or phenyl substituted by lower alkyl, lower alkoxy or halo.

Most preferred of the compounds of Formula IV are those wherein $R_4$ and $R_5$ are each independently hydrogen, halo or $NO_2$ and R is halo-lower alkyl.

Particularly valuable compounds of Formula III are:

(1-ethyl-piperidin-3-yl)-(6-iodo-2-p-tolyl-quinazolin-4-yl)-amine, (1-ethyl-piperidin-3-yl)-(6-iodo-2-(4-methoxy-phenyl)-quinazolin-4-yl)-amine,

[2-(4-chloro-phenyl)-6-iodo-quinazolin-4-yl]-(1-ethyl-piperidin-3-yl)-amine, (2-tert-butyl-6-iodo-quinazolin-4-yl)-(1-ethyl-piperidin-3-yl)-amine, (1-ethyl-piperidin-3-yl)-(6-iodo-2-phenyl-quinazolin-4-yl)-amine, (1-ethyl-piperidin-3-yl)-(6-iodo-2-trichloromethyl-quinazolin-4-yl)-amine,

[3-(6-iodo-2-trichloromethyl-quinazolin-4-ylamino)-piperidin-1-yl]-acetic acid, (1-ethyl-piperidin-3-yl)-(6-chloro-2-trichloromethyl-quinazolin-4-yl)-amine, (1-ethyl-piperidin-3-yl)-(6-nitro-2-trichloromethyl-quinazolin-4-yl)-amine, (1-ethyl-piperidin-3-yl)-(2-trichloromethyl-quinazolin-4-yl)-amine, (1-ethyl-piperidin-3-yl)-(7-chloro-2-trichloromethyl-quinazolin-4-yl)-amine, (1-ethyl-piperidin-3-yl)-(6-iodo-2-trifluoromethyl-quinazolin-4-yl)-amine, and (1-ethyl-pyrrolidin-2-yl-methyl)-(6-iodo-2-trichloromethyl-quinazolin-4-yl)-amine.

The compounds of the present invention are valuable inhibitors of endothelin converting enzyme. The tests employed indicate that such compounds possess inhibitory activity towards an endothelin converting enzyme.

SCREENING OF ENDOTHELIN CONVERTING ENZYME (ECE) INHIBITORS

Cell Culture

A permanent human cell line (EA.hy926), derived by fusing human umbilical vein endothelial cells with the permanent human cell line A549 (derived from a human lung carcinoma), was cultured as described, except that the medium also contained HAT supplements (100 µM hypoxanthine, 0.4 µM aminopterin, 16 µM thymidine). Edgell, C.-J. S., McDonald, C. C., and Graham, J. B. (1983) Proc. Natl. Acad. Sci. USA 80, 3734–3737. Cells from passages 40 to 50 were used. Subcultures were prepared by treating confluent cells with trypsin (0.5%) and seeded either onto 24 well plates for a cell-based assay or onto roller bottles for a partial purification of the enzyme.

Partial Purification of ECE from EA.hy926

All operations were carried out at 0°–4° C. unless otherwise noted. The cells in each roller bottle were washed with phosphate-buffered saline and gently scraped. These cells were washed further with phosphate-buffered saline followed by 10 mM Tris-HCl, pH 7.5/0.25M sucrose/20 mM KCl (buffer A) and frozen immediately in liquid nitrogen. The cells from 150 roller bottles were suspended in 100 mL of buffer A containing protease inhibitors cocktail (1 mM phenylmethylsulfonyl fluoride/0.05 mM pepstatin A/0.1 mM leupeptin) and were homogenized via nitrogen cavitation (600 psi, 10 min.) and centrifuged at 5,000×g for 20 min. This process was repeated with the pellet resuspended in 100 mL of buffer A containing protease inhibitors cocktail. The combined supernatant was then centrifuged at 20,000×g for 35 min. The resulting supernatant was further centrifuged at 100,000×g for 1 h. The pellet was washed with 120 mL of 20 mM Tris-HCl, pH 7.5/0.02% NaN$_3$ (buffer B), resuspended in 40 mL of buffer B containing 0.5% Triton X-100 (hydrogenated) and protease inhibitors cocktail, and was stirred gently for 1 h (membrane fraction). The clear supernatant was obtained by centrifugation at 100,000×g for 1 h (detergent extract). For *Ricinus communis* agglutinin chromatography (RCA-I), the detergent extract was applied at a flow rate of 0.15 ml/min onto a 4-ml RCA-I column (0.5×20 cm) equilibrated with 50 mM Tris-HCl, pH 7.2/50 mM NaCl/0.02% NaN$_3$/0.2% Triton X-100 (hydrogenated) (buffer C) including protease inhibitors cocktail. The column was washed with the equilibration buffer until A$_{280\ nm}$ of the eluate was less than 0.03, and the activity was eluted with buffer C containing 0.5M galactose at a flow rate of 0.15 ml/min. Fractions of 4 mL were collected and peak fractions were pooled (RCA-I fraction, 20 mL) (see Table II).

The above procedure yielded 35.6-fold purification of ECE from the membrane fraction (Table II) which was used for the screening of ECE inhibitors. This enzyme has a neutral pH optimum and is phosphoramidon-sensitive with an IC$_{50}$ value of 1.8 µM. The enzyme is also inhibited by EDTA, EGTA, and 1,10-phenanthroline but was not inhibited by pepstatin A, leupeptin, phenylmethlysulfonyl fluoride, soybean trypsin inhibitor, E-64, bestatin, captopril, enalaprilat or thiorphan.

The cell line, EA.hy926, contains neutral endopeptidase 24.11 (NEP 24.11) which also cleaves big ET-1 to ET-1 and c-terminal fragment (manuscript submitted). Therefore, for all ECE assays, 100 µM thiorphan or 100 nM phosphoramidon was added. Under these conditions, NEP 24.11 is completely inhibited without affecting the ECE activity. All the data were obtained in the linear range of time-course curves.

TABLE II

Partial Purification of ECE from EA.hy926[a]

| Fraction | Total Volume mL | Protein Concentration Absorbance (280 nm) | Total Activity untis[b] | Specific Activity units/mL/ A$_{280\ nm}$ |
|---|---|---|---|---|
| Membrane | 40.0 | 0.902[c] | 382 | 1.1 |
| Detergent extract | 39.4 | 0.387[c] | 301 | 2.0 |
| RCA-I | 20.0 | 0.386 | 275 | 35.6 |

[a]ECE was partially purified from EA.hy926 grown in 150 roller bottles to confluency.
[b]One unit of enzyme is defined as the amount generating 1 pmol of immunoreactive (ir) ET-1 per min.
[c]Absorbance shown was measured after tenfold dilution.

ECE Assay

The assay measured the production of ET-1 essentially as described with minor modifications. Ahn, K., Beningo, K., Olds, G., and Hupe, D. (1992) *Proc. Natl. Acad. Sci. USA* 89, 8606–8610. The typical reaction mixture (50 µl) contained 10 µM big ET-1, 100 mM Hepes-KOH (pH 7.0), 0.25%. Triton X-100, 0.01% NaN$_3$, 0.1 mM thiorphan, 0.2 mM phenylmethylsulfonyl fluoride, 0.02 mM pepstatin A, 0.1 mM leupeptin, and the enzyme. For screening inhibitors, the indicated concentration of a drug (or DMSO for control) dissolved in DMSO was added and the final concentration of DMSO was kept at 3%. After incubation for 1.5 hours at 37° C., the reaction was stopped by the addition of EDTA to give a final concentration of 10 mM. This final mixture was diluted with 60 mM KP$_+$, pH 7.4/10 mM EDTA/8 mM NaN$_3$/0.1% bovine serum albumin/0.1% Tween 20/3% DMSO (buffer D) and the generated ET-1 was measured by radioimmunoassay (RIA).

Radioimmunoassay (RIA)

ET-1 was measured by radioimmunoassay (RIA) as described previously with minor modifications. Ahn, K., Beningo, K., Olds, G., and Hupe, D. (1992) *Proc. Natl. Acad. Sci, USA*, 89, 8606–8610. Briefly, the RIA mixture (250 µl) contained the antibody against ET-1, an ET-1 sample, and [$^{125}$I] ET-1 (15000 cpm) in buffer D. For the analysis of ET-1 from cell based assays, the final 6% bovine serum albumin was added. The order of additions was ET-1 sample, antibody, and then [$^{125}$I]ET-1. After incubation at 4° C. for 16 hr, unbound ET-1 was co-precipitated by the addition of charcoal (2.4%, wt/vol)/dextran (0.24%, wt/vol) suspension (125 µl) in 60 mM KP$_i$ pH 7.4/10 mM EDTA/8 mM NaN$_3$/0.25% gelatin (wt/vol). The amount of immunoreactive (ir) ET-1 was measured by counting the supernatant and determined from the standard curve. The cross reactivity to big ET-1 was less than 0.01% and the detection limit was 1 fmol.

TABLE III

Biological Activity of Compounds of the Present Invention

| Example | IC$_{50}$ µM |
|---|---|
| 1 | 4.2 ± 0.5 |
| 2 | 9.2 ± 0.8 |
| 3 | 14.1 ± 1.5 |
| 4 | 29.1 ± 5.4 |
| 5 | 17.6 ± 1.7 |
| 6 | 29.6 ± 6 |
| 7 | 22.1 ± 4.8 |
| 8 | 11.1 ± 2.7 |
| 9 | 3.7 ± 1.6 |
| 10 | 25.4 ± 4.2 |
| 11 | 12.4 ± 1 |
| 12 | 11.1 ± 1.7 |
| 13 | 66.6 ± 11.8 |
| 14 | 75.5 ± 11.6 |
| 15 | 11.1 ± 1.7 |
| 16 | 8.4 ± 1.4 |
| 17 | 2.3 ± 0.3 |

Procedure for a Cell-Based Assay

EAhy926 cells (0.2"4×10$^4$) were seeded into 24-plates and cultures as described above. At 90%–100% confluence, the cells were washed with the same media and treated with medium containing drugs (or DMSO for control) at indicated concentrations and 10 µM phosphoramidon (for NEP 24.11 inhibition) (0.5 ml/well). The final DMSO concentration for all experiments was 0.5%. After incubation for 18–24 hours, the medium was collected and centrifuged at 10,000×g for 5 min in order to remove cell debris. The resulting supernatant was used for the measurement of ET-1 by RIA. The ET-1 level from these samples were measured by RIA previously described. Ahn, K., Beningo, K., Olds, G., and Hupe, D. (1992) Proc. Natl. Acad. Sci. USA 89, 8606–10.

TABLE IV

| Example | IC$_{50}$ (µM) |
|---|---|
| 1 | 6.6 ± 1.5 |
| 3 | 14.4 ± 1.1 |

The compounds of the present invention my be prepared generally as shown in Scheme I. Although Scheme I illustrates the preparation of compounds where A is N, step (a) may also be carried out when A is CH or S(O)$_n$ as defined above.

SCHEME I

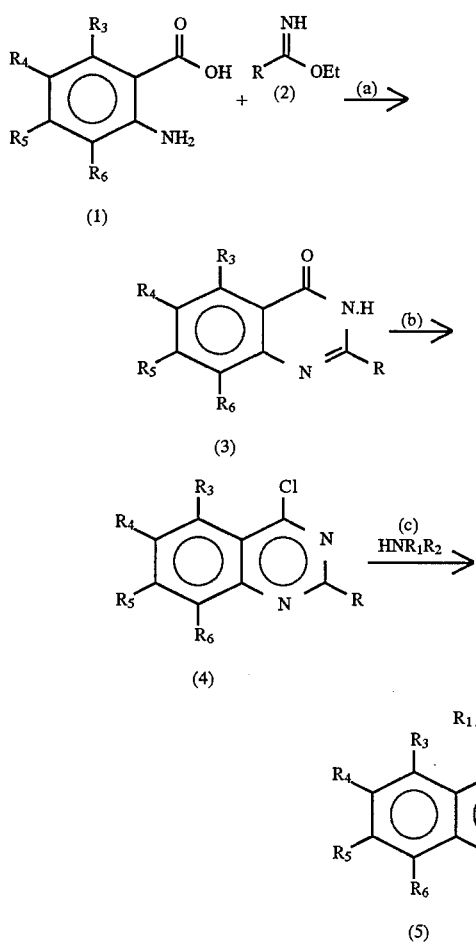

Step (a) involves reacting anthranilic acid derivative of formula (1) with appropriately substituted imidates depicted in formula (2) in ethanol or other hydroxylated solvents at elevated temperatures preferably between 50°–70° C. The reaction is carried out for 8–24 hours preferably 16 to 17 hours. The product, substituted quinazoline 4-one is shown in formula (3) separates as a crystalline solid. The reaction mixture is cooled below room temperature preferably between 0°–5° C. and filtered. The product is washed with water until neutral and air-dried.

Step (b) involves reacting quinazoline-4-one depicted in formula (3) with chlorinating agents like phosphorus oxychloride, phosphorus pentachloride or thionyl chloride, preferably phosphorus oxychloride at elevated temperatures preferably at the reflux for periods ranging from 6 to 20 hours preferably 14 to 16 hours. The reaction mixture is cooled to ambient temperatures and poured continuously over crushed ice under vigorous stirring keeping temperatures below 5° C. The solid which separates is filtered and washed with water until neutral. The air-dried solid is extracted with inert solvents like benzene, toluene or xylene preferably toluene and filtered. The filtrate is evaporated in vacuo to give 4-chloro-quinazolines shown in formula (4).

Step (c) involves reacting 4-chloro-quinazolines depicted in formula (4) with various primary or secondary amines (1–2 equivalents) in ethereal solvents preferably diethyl ether at temperatures between 15°–25° C. preferably ambient temperature for periods of 16–24 hours preferably 20 hours to give a suspension. The suspension is filtered to give 4-amino quinazolines shown in formula (5) as a solid. In some cases, the reaction mixture is poured in water and the product extracted in ethyl acetate or chloroform, preferably ethyl acetate. The organic extracts are collected and washed with water until excess amine is removed and dried over magnesium sulfate. The solvent is removed under vacuo and 4-aminoquinazolines (5) are isolated by chromatography, preferably silica gel using petroleum ether and ethyl acetate mixture in the ratio of 8:2 to 1:1.

Starting anthranilic acids and compounds of formula (2) may be purchased commercially or prepared from commercially available materials by known methods.

Schemes II, III and IV illustrate preferred process routes to particular compounds of the present invention. However, these routes may also be generally used to prepare compounds of the present invention with certain limitations. For example, Scheme II shows a preferred route to compounds of the invention in general but where R is trichloromethyl. Scheme III also can be used generally to prepare compounds of the present invention but where R is halo-lower alkyl, in this case, trifluoromethyl. Scheme IV illustrates the preferred route to compounds of Formula III starting with 3-aminopyridine.

SCHEME II

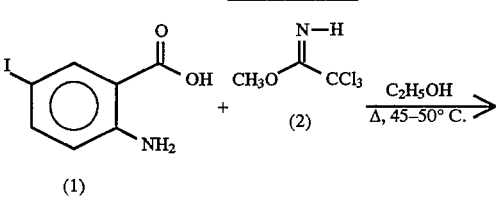

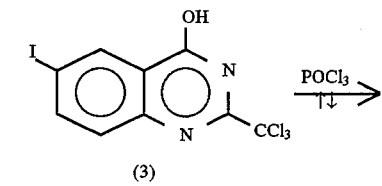

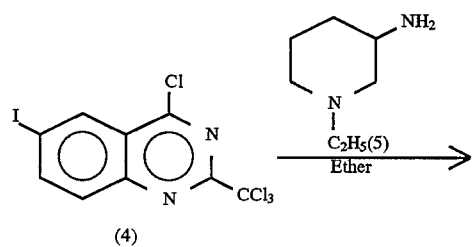

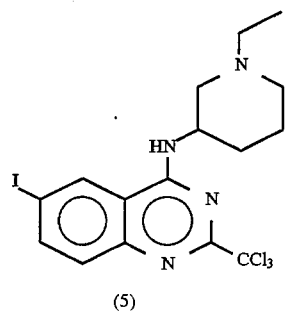

SCHEME III
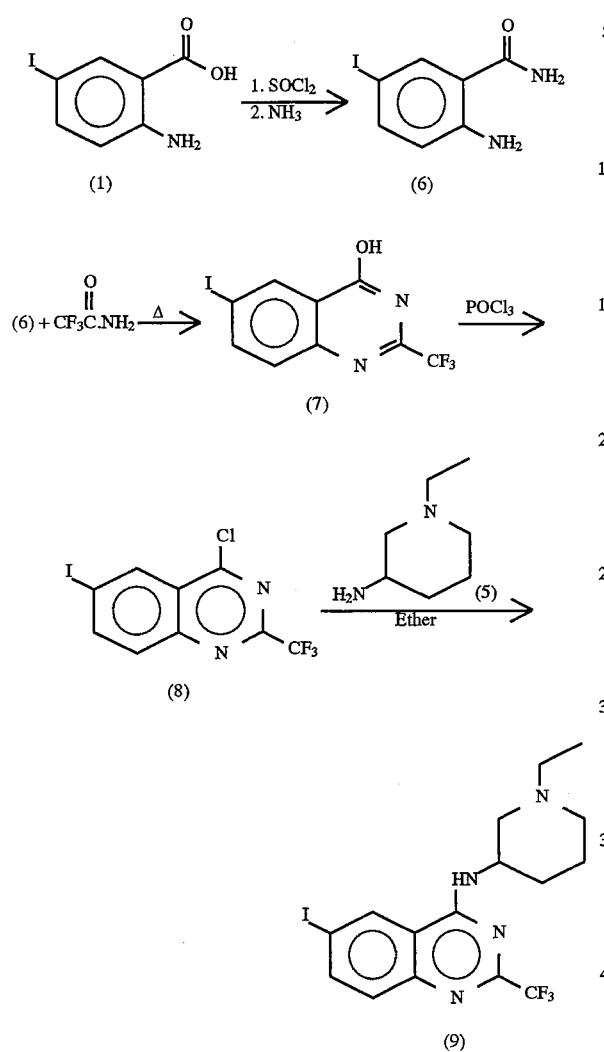
SCHEME IV
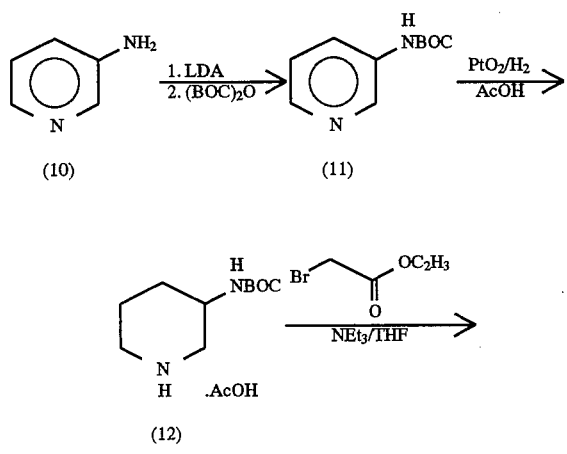
-continued
SCHEME IV
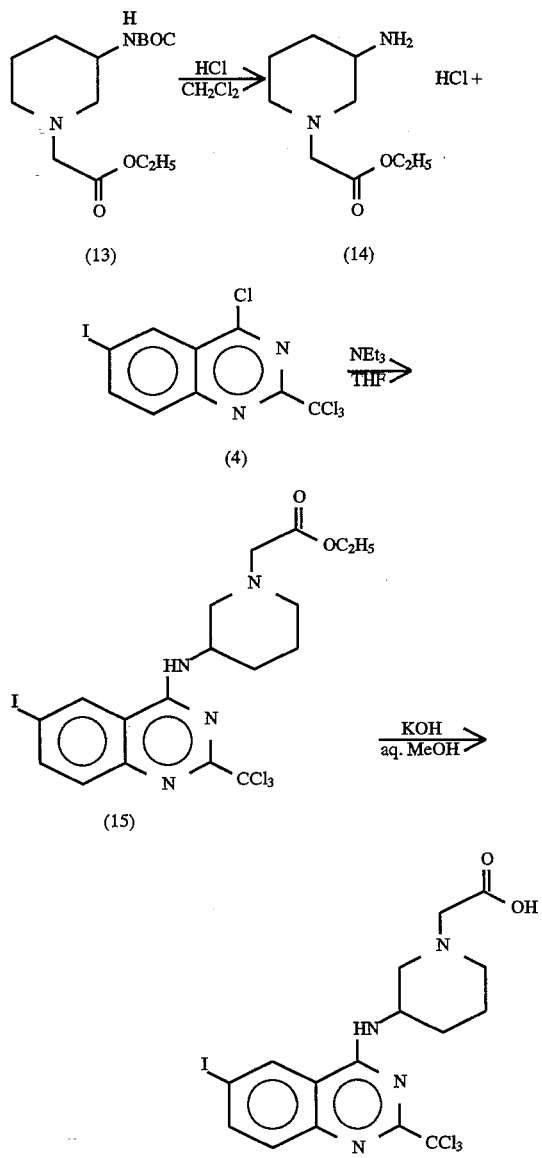
SCHEME V
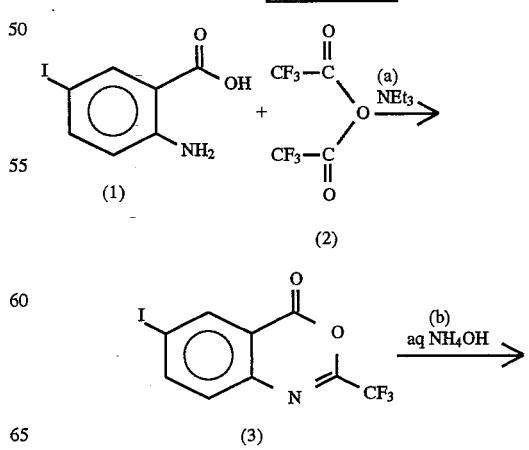

-continued
SCHEME V

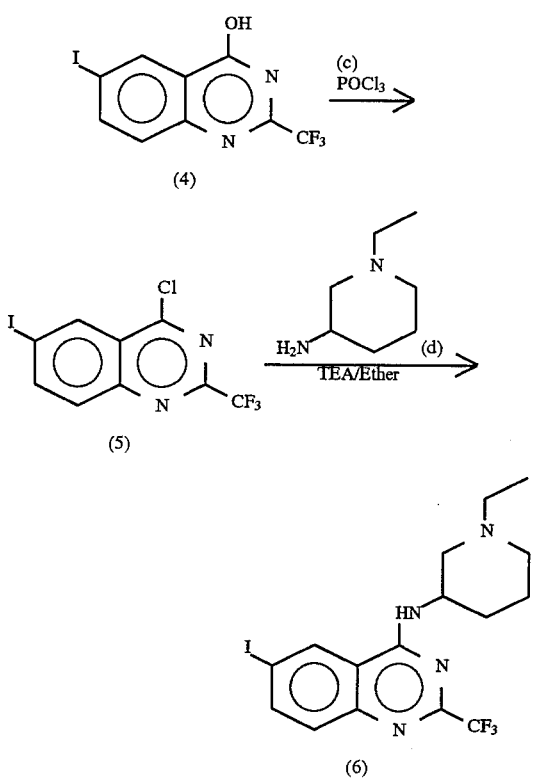

Scheme V illustrates an alternate route for the synthesis of 2-substituted 4-chloro-quinazoline.

Step (a) involves reacting anthranilic acid derivative of Formula (1) with appropriately substituted anhydrides (2), in this case trifluoroacetate anhydride, in the presence of tertiary bases like triethylamine at elevated temperatures preferably at the reflux for 1–6 hours, preferably 2 hours. The volatile components are removed under reduced pressure and the residue treated with an ethereal solvent like diethyl ether and water. The ethereal layer was separated, dried over MgSO$_4$ and concentrated to give the appropriate benzo[d] [1.3]oxazin-4-one derivative as the product.

Step (b) involves reacting benzo[d][1.3]oxazin-4-one depicted in Formula 3 with saturated ammonia water at elevated temperatures preferably at 40° C. for 4–8 hours, preferably 5 hours. The reaction mixture is cooled below room temperature preferably between 0°–5° C. and the precipitate obtained, filtered and dried under reduced pressure (0.1–0.5 mm). The product is crystallized from a mixture of petroleum ether and ethyl acetate.

Step (c) and step (d) are carried out as described in step (b) and (c) of Scheme I.

The compounds of the present invention can be prepared and administered in a wide variety of oral and parenteral dosage forms. Thus, the compounds of the present invention can be administered by injection, that is, intravenously, intramuscularly, intracutaneously, subcutaneously, intraduodenally, or intraperitoneally. Also, the compounds of the present invention can be administered by inhalation, for example, intranasally. Additionally, the compounds of the present invention can be administered transdermally. It will be obvious to those skilled in the art that the following dosage forms may comprise as the active component, either a compound of the present invention, such as a compound of Formula I, II or III or a corresponding pharmaceutically acceptable salt of a compound of Formula I, II or III.

For preparing pharmaceutical compositions from the compounds of the present invention, pharmaceutically acceptable carriers can be either solid or liquid. Solid form preparations include powders, tablets, pills, capsules, cachets, suppositories, and dispersible granules. A solid carrier can be one or more substances which may also act as diluents, flavoring agents, binders, preservatives, tablet disintegrating agents, or an encapsulating material.

In powders, the carrier is a finely divided solid which is in a mixture with the finely divided active component.

In tablets, the active component is mixed with the carrier having the necessary binding properties in suitable proportions and compacted in the shape and size desired.

The powders and tablets preferably contain from 5% or 10% to about 70% of the active compound. Suitable carriers are magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. The term "preparation" is intended to include the formulation of the active compound with encapsulating material as a carrier providing a capsule in which the active component with or without other carriers, is surrounded by a carrier, which is thus in association with it. Similarly, cachets and lozenges are included. Tablets, powders, capsules, pills, cachets, and lozenges can be used as solid dosage forms suitable for oral administration.

For preparing suppositories, a low melting wax, such as a mixture of fatty acid glycerides or cocoa butter, is first melted and the active component is dispersed homogeneously therein, as by stirring. The molten homogenous mixture is then poured into convenient sized molds, allowed to cool, and thereby to solidify.

Liquid form preparations include solutions, suspensions, and emulsions, for example, water or water propylene glycol solutions. For parenteral injection liquid preparations can be formulated in solution in aqueous polyethylene glycol solution.

Aqueous solutions suitable for oral use can be prepared by dissolving the active component in water and adding suitable colorants, flavors, stabilizing, and thickening agents as desired.

Aqueous suspensions suitable for oral use can be made by dispersing the finely divided active component in water with viscous material, such as natural or synthetic gums, resins, methylcellulose, sodium carboxymethylcellulose, and other well-known suspending agents.

Also included are solid form preparations which are intended to be converted, shortly before use, to liquid form preparations for oral administration. Such liquid forms include solutions, suspensions, and emulsions. These preparations may contain, in addition to the active component, colorants, flavors, stabilizers, buffers, artificial and natural sweeteners, dispersants, thickeners, solubilizing agents, and the like.

The pharmaceutical preparation is preferably in unit dosage form. In such form the preparation is subdivided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form.

The quantity of active component in a unit dose preparation my be varied or adjusted from 0.1 mg to 200 mg preferably 0.5 mg to 100 mg according to the particular application and the potency of the active component. The composition can, if desired, also contain other compatible therapeutic agents.

In therapeutic use as inhibitors of endothelin converting enzyme the compounds utilized in the pharmaceutical method of this invention are administered at the initial dosage of about 0.01 mg to about 500 mg/kg daily. A daily dose range of about 0.01 mg to about 100 mg/kg is preferred. The dosages, however, may be varied depending upon the requirements of the patient, the severity of the condition being treated, and the compound being employed. Determination of the proper dosage for a particular situation is within the skill of the art. Generally, treatment is initiated with smaller dosages which are less than the optimum dose of the compound. Thereafter, the dosage is increased by small increments until the optimum effect under the circumstances is reached. For convenience, the total daily dosage may be divided and administered in portions during the day, if desired.

The following nonlimiting example illustrates the inventors' preferred methods for preparing the compounds of the invention.

EXAMPLE 1

(1-Ethyl-piperidin-3-yl)-(6-iodo-2-trichloromethyl-quinazolin-4-yl)-amine, monohydrochloride Step 1: Preparation of 6-iodo-2-trichloromethyl-1,2-dihydro-quinazolin-4-one To a solution of 5-iodoanthranilic acid (131.5 g, 500 mmol) in ethanol (700 mL), 2,2,2-trichloroacetimidate (88.2 g, 500 mmol) was added. The reaction mixture was heated at 45° C. for 3 days under stirring. The solid formed was filtered and washed with fresh ethanol and air-dried. Yield 129.51 g (66.4%). Mp 224°–225° C. $^1$H-NMR (DMSO) 7.59 (d, 1 h, J=8.6 Hz), 8.21 (dd, 1H, J=2 Hz, J=7.5 Hz), 8.44, 1H, J=1.9 Hz), 13.55 (bs, 1H).

MS(CI); $M^+$=499. CHN calculated for $C_{16}H_{18}Cl_3IN_4 \cdot HCl$; C: 35.84, H: 3.57, N: 10.45; Found: C: 35.81, H: 3.35, N: 10.44.

Step 2: Preparation of 6-iodo-4-chloro-2-trichloromethyl quinazolin

A suspension of 6-iodo-2-trichloromethyl-1,2-dihydro-quinazolin-4-one (38.9 g=100 mmol) in $POCl_3$ (500 mL) was heated to reflux for 12 hours. The homogeneous solution was cooled and excess $POCl_3$ was distilled under vacuum. Viscous oil obtained was poured over crushed ice and triturated vigorously to give grey solid, which was dissolved in toluene (200 mL), filtered and evaporated under vacuo to give off-white crystalline solid. Mp 154°–155° C. Elemental Analysis: Calculated for $C_9H_3Cl_4IN_2$, C: 26.50, H, 0.74, N: 6.87; Found: C: 26.15, H: 0.79, N. 6.68.

Step 3: Preparation of (1-ethyl-piperidin-3-yl)-(6-iodo-2-trichloromethyl-quinazolin-4-yl)-amine, monohydrochloride 6-iodo-4-chloro-2-trichloromethyl-quinazolin (8.14 g, 20 mmol) was dissolved in ether (anhydrous 200 mL) under stirring at rt. To this solution 3-amino-1-ethyl-piperidine (2.56 g, 20 mmol) in ether (anhydrous 30 mL) was added at 0° C. The reaction mixture was allowed to warm to rt overnight. Buff colored solid separated which was filtered, washed with ether (200 mL) and air dried. Crude yield: 5.1 g. The crude material was suspended in MeOH and stirred vigorously for 0.5 h and filtered. The solid was dried in vacuo (0.01 mm). Yield: 3.72 g, (34.7%). Mp 265°–266° C.

In a process analogous to Example 1 using appropriate starting materials, the corresponding compounds of Formula I are prepared as follows:

EXAMPLE 2

(1-Ethyl-piperidin-3-yl)-(6-iodo-2-phenyl-quinazolin-4-yl)-amine. MS (CI) M+1=459, CHN calculated for $C_{21}H_{23}IN_4$; C: 55.03; H: 5.06; N: 12.22; Found: C: 54.99; H: 5.11, N: 11.82.

EXAMPLE 3

(1-Ethyl-piperidin-3-yl)-(6-chloro-2-trichloromethyl-quinazolin-4-yl)-amine. Mp 274°–276° C., CHN calculated for $C_{16}H_{18}Cl_4N_4 \cdot HCl$, C: 43.22, H: 4.30, N: 12.00; Found: C: 43-23, H: 4.16 N: 12.47.

EXAMPLE 4

(1-Ethyl-piperidin-3-yl)-(6-nitro-2-trichloromethyl-quinazolin-4-yl)-amine. MS (CI) M+1=418. CHN calculated for $C_{14}H_{18}Cl_3N_5O_2$. HCl; C: 42.22, H: 4.21, N: 15.39, Found: C: 42.30; H: 4.19, N: 15.01.

EXAMPLE 5

(2-tert-Butyl-6-iodo-quinazolin-4-yl)-(1-ethyl-piperidin-3-yl)-amine, MS (CI) M+1=439. CHN calculated for $C_{19}H_{27}IN_4$.

EXAMPLE 6

N-(6-Iodo-2-trichloromethyl-quinazolin-4-yl)-ethane-1,2-diamine hydrochloride, MS (CI) M+1 36.5=431.

EXAMPLE 7

N-(6-Iodo-2-trichloromethyl-quinazolin-4-yl)-$N^1$-methyl-ethane-1,2-diamine. MS (CI) M+1=444.

EXAMPLE 8

N-(6-Iodo-2-trichloromethyl-quinazolin-4-yl)-$N^1,N^1$-dimethyl-ethane-1,2-diamine. MS (CI) M+1=459.

EXAMPLE 9

(6-Iodo-2-trichloromethyl-quinazolin-4-yl)-(2-piperidin-1-yl-ethyl)-amine, mp 254°–255° C. (dec), MS (CI): m/z 499 $(MH)^+$.

EXAMPLE 10

(6-Iodo-2-trichloromethyl-quinazolin-4-yl)-(2-morpholin-4-yl-ethyl)-amine, mp 182°–183° C. (dec), MS(CI): m/z 501 $(MH)^+$.

EXAMPLE 11

(1-Ethyl-pyrrolidin-2-yl-methyl)-(6-iodo-2-trichloromethyl-quinazolin-4-yl)-amine, mp 147°–153° C., MS (CI): m/z 499 $(MH)^+$.

EXAMPLE 12

(1-Aza-bicyclo[2,2,2,]oct-3-yl)-(6-iodo-2-trichloromethyl-quinazolin-4-yl)-amine, mp >280° C. (dec), MS (CI): m/z 497 $(MH)^+$.

EXAMPLE 13

N-(7-Chloro-2-trichloromethyl-quinazolin-4-yl)-N',N'-diisopropyl-ethane-1,2-diamine. mp 199°–203° C. Elemental analysis calc'd for $C_{17}H_{22}N_4Cl_5 \cdot HCl$: C: 44.33; H: 5.3; N: 12.16; Found C: 44.34; H: 5.30; N: 12.26.

EXAMPLE 14

[3-(6-Iodo-2-trichloromethyl-quinazolin-4-ylamino)-piperidin-1-yl]-acetic acid potassium salt. Elemental analysis calc'd for $C_{16}H_{15}N_4O_2Cl_3IK$: C: 33.83; H: 2.64; N: 9.86 Found C: 33.68; H: 3.01; N: 9.72.

EXAMPLE 15

(1-Aza-bicyclo[2.2.2]oct-3-yl)-(6-iodo-2-trichloromethyl-quinazolin-4-yl)-amine monohydrochloride, mp >280° C. (dec), MS(CI): M+1=498.

EXAMPLE 16

N'-(6-Iodo-2-trichloromethyl-quinazolin-4-yl)-N,N,N", N"-tetramethyl-propane-1,2,3-triamine monohydrochloride, mp 207°–208° C. (dec), MS(CI): M+1=517.

EXAMPLE 17

(1-Ethyl-piperidin-3-yl)-(6-iodo-2-trifluoromethyl-quinazolin-4-yl)-amine.

Step 1: 6-iodo-2-trifluoromethyl-benzo[d][1,3] oxazin-4-one 5-iodo-2-aminobenzoic acid (2.1 g, 8 mmole) was mixed with trifluoroacetic anhydride (12 g, 57 mmole) and 2 mL of triethyl amine, heated to reflux for 2 h. The solvent was removed under reduced pressure, the residue was stirred with 25 mL of ether and 5 mL of water. The organic layer was separated, dried and concentrated to give 1.92 g of product, mp 131°–132° C., MS (CI): m/z 342 (MH)$^+$.

Step 2: 6-iodo-2-trifluoromethyl-3H-quinazolin-4-one 6-iodo-2-trifluoromethyl-benzo[d][1,3] oxazin-4-one (0.6 g, 1.76 mmole) was stirred with 25 mL of concentrated ammonia water at 40° C. for 5 h, cooled to 0° C., the precipitate was filtered and dried under vacuo. The product was recrystallized from ethyl acetate and haxanes to give 0.58 g, mp >255° C. (sub), MS (CI): m/z 341 (MH)$^+$.

Step 3: 6-iodo-2-trifluoromethyl-4-chloroquinazoline 6-iodo-2-trifluoromethyl-3H-quinazolin-4-one (3.1 g, 9.1 mmole) was mixed with 20 mL of POCl$_3$, heated to reflux for 3 h, removed most of unreacted POCl$_3$ under vacuo. The residue was extracted with 15 mL of NaHCO$_3$(sat) and 200 mL of ether, ether layer was dried with MgSO$_4$ and concentrated to give the light yellow solid 3.05 g, mp 145°–146° C., MS (CI): m/z 359 (MH)$^+$.

Step 4: (1-ethyl-piperidin-3-yl)-(6-iodo-2-trifluorom ethyl-quinazolin-4-yl)-amine 6-iodo-2-trifluoromethyl-4-chloroquinazoline (1.5 g, 4.2 mmole) was mixed with 3-amino-ethyl piperidine (0.62 g, 4.8 mole) and triethyl amine in 200 mL of ether. The product was isolated as hydrochloride salt by previous method, to give 1.25 g, mp 296°–297° C. (dec), MS (CI): m/z 359 (MH)$^+$.

We claim:

1. A compound of the formula

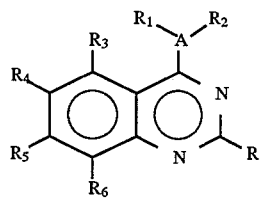

wherein A is N;
R is lower alkyl,
  halo-lower alkyl,
  aryl, wherein aryl is unsubstituted or substituted,
  aryl-lower alkyl, wherein aryl is unsubstituted or substituted,
  heteroaryl, wherein heteroaryl is 2- or 3-thienyl, 2- or 3-furanyl, 2- or 3-pyrrolyl, 2-, 4-, or 5-imidazolyl, 3-, 4-, or 5-pyrazolyl, 2-, 4-, or 5-thiazolyl, 3-, 4-, or 5-isothiazolyl, 2-, 4-, or 5-oxazolyl, 3-, 4-, or 5-isoxazolyl, 3- or 5-1,2,4-triazolyl, 4- or 5-1,2,3-triazolyl, tetrazolyl, 2-, 3-, or 4-pyridinyl, 3-, 4-, or 5-pyridazinyl, 2-pyrazinyl, 2-, 4-, or 5-pyrimidinyl, 2-, 3-, 4-, 5-, 6-, 7-, or 8-quinolinyl, 1-, 3-, 4-, 5-, 6-, 7-, or 8-isoquinolinyl, 2-, 3-, 4-, 5-, 6- or 7-indolyl, N-formyl-2-, 3-, 4-, 5-, 6-, or 7-indolyl, 2-, 3-, 4-, 5-, 6-, or 7-benzo[b]thienyl, 2-, 4-, 5-, 6-, or 7-benzoxazolyl, 2-, 4-, 5-, 6-, or 7-benzimidazolyl, or 2-, 4-, 5-, 6-, 7-benzothiazolyl, unsubstituted or substituted by 1 to 2 substituents selected from the group consisting of lower alkyl, lower alkoxy, trifluoromethyl, nitro, halogen, CN, SO$_3$H, SO$_2$NH$_2$, SO$_2$CH$_3$, COOH, COO-lower alkyl, CONH$_2$, CO-lower alkyl, NH$_2$, NH-lower alkyl, N,N-di-lower alkyl, NH-aralkyl, N-di-aralkyl, and N,N-lower alkyl-aralkyl, or heteroaryl-lower alkyl wherein heteroaryl is as defined above;

R$_1$ is a 5–7 membered saturated heterocyclic ring fused to a benzene rang, wherein the fused 5–7 membered saturated heterocyclic ring is selected from the group consisting of: dihydrobenzofuran, dihydroisobenzofuran, dihydrobenzothiophene, dihydroisobenzothiophene, indoline, isoindoline, chroman, isochroman, thiochroman, isothiochroman, tetrahydroquinoline, and tetrahydroisoquinoline, wherein said heterocyclic ring is attached directly to A or through an alkyl group linking A with the ring at a carbon atom, a 5–7 membered saturated heterocyclic ring optionally interrupted by a second heteroatom selected from nitrogen, oxygen and sulfur wherein the 5–7 membered heterocyclic ring is selected from the group consisting of: pyrrolidine, pyrrazolidine, imidazolidine, oxazolidine, thiaoxazolidine, piperidine, piperazine, morpholine, thiamorpholine, and homopiperidine, and wherein the second heteroatom atom is nitrogen, said second nitrogen atom may be substituted by alkyl, carboxyalkyl or lower alkyl-carboxyalkyl and wherein the carbon atoms of the above 5–7 membered heterocyclic ring may be substituted independently by alkyl, amine, aminoalkyl, monoalkylaminoalkyl, dialkylamino-alkyl, carboxy, carboxyalkyl, alkylcarboxyalkyl, thio, thioalkyl, alkylthioalkyl, hydroxy, hydroxyalkyl, alkoxy or alkoxyalkyl wherein said heterocyclic ring is attached directly to A or through an alkyl group linking A with the ring at a carbon atom or 5,6 or 6,6-membered heterocyclic bicyclic rings, having at least 1 heteroatom, selected from the group consisting of 1-aza-bicyclo[3,2,1]octane and 1-aza-bicyclo[2.2.2] octane said heterocyclic bicyclic rings being optionally substituted by
alkyl,
amino,
aminoalkyl,
monoalkylaminoalkyl,
dialkylaminoalkyl,
carboxy,
carboxyalkyl,
alkylcarboxyalkyl,
thio,
thioalkyl,
alkylthioalkyl, hydroxy,
hydroxyalkyl,
alkoxy, or
alkoxyalkyl,
wherein said rings are attached directly to A or through an alkyl group linking A and the ring at a carbon atom;

$R_2$ is a hydrogen atom or lower alkyl;

$R_3$, $R_4$, $R_5$ and $R_6$ are each independently hydrogen, halo, lower alkyl, cycloalkyl, halo-lower alkyl, lower alkoxy, hydroxyalkyl, aminoalkyl, lower alkyl aminoalkyl, di-lower alkyl aminoalkyl, nitro, cyano, $SO_2NR_{11}R_{12}$, $SO_2R_9$, $CO_2R_9$, $CONR_{11}R_{12}$, or $NR_{11}R_{12}$ in which $R_{11}$ and $R_{12}$ are each independently hydrogen, lower alkyl, aryl as defined above, heteroaryl as defined above or aralkyl, or a pharmaceutically acceptable acid addition or base salt thereof; with the following provisos:

(a) when $R_1$ is morpholine or piperazine R is not 5-nitro-2-pyrrolyl, 5-nitro-2-imidazolyl, 5-nitro-2-thiazolyl or 5-nitro-2-oxazolyl;

(b) when $R_1$ is a pyrrolidine optionally substituted by alkyl or carboxy-lower alkyl and $R_3$ and $R_6$ are as defined above, then R is halo-lower alkyl, aryl as defined above, aryl-lower alkyl, heteroaryl as defined above, or heteroaryl-lower alkyl wherein heteroaryl is as defined above;

(c) when $R_1$ is piperidine R cannot be lower alkyl; and (d) when $R_1$ is 1-aza-bicyclo[3,2,1]octane or 1-aza-bicyclo[2.2.2]octane R is not lower alkyl.

2. A pharmaceutical composition adapted for administration as an inhibitor of endothelin converting enzyme comprising a therapeutically effective amount of compound of claim 1 in admixture with a pharmaceutically acceptable carrier.

3. A compound according to the formula

III wherein A is N; and q is 0, 1 or 2;

B, C, D and E are $CH_2$ or $NR_{13}$ in which only one of B, C, D or E is $NR_{13}$ wherein $R_{13}$ is hydrogen, lower alkyl, aralkyl, —$(CH_2)_m CO_2R_9$ in which $R_9$ is hydrogen or lower alkyl, or —$(CH_2)_m NR_9R_{10}$ in which $R_9$ and $R_{10}$ are each independently hydrogen or lower alkyl and m is an integer of 0 to 6, p is an integer from 0 to 2, and r is an integer from 0 to 2;

R is lower alkyl,
halo-lower alkyl,
phenyl or phenyl-lower alkyl in which phenyl is unsubstituted or substituted by lower alkyl, lower alkoxy, trifluoromethyl, halo, $NO_2$, CN, $SO_3H$, $SO_2NH_2$, $SO_2CH_3$, $COOR_9$ in which $R_9$ is hydrogen or lower alkyl, $CONR_9R_{10}$ wherein $R_9$ and $R_{10}$ are each independently hydrogen, or $NR_{11}R_{12}$ wherein $R_{11}$ and $R_{12}$ are each independently hydrogen, lower alkyl, or aralkyl,
heteroaryl wherein heteroaryl is 2- or 3-thienyl, 2- or 3-furanyl, 2- or 3-pyrrolyl, 2-, 4-, or 5-imidazolyl, 3-, 4-, or 5-pyrazolyl, 2-, 4-, or 5-thiazolyl, 3-, 4-, or 5-isothiazolyl, 2-, 4-, or 5-oxazolyl, 3-, 4-, or 5-isoxazolyl, 3- or 5-1,2,4-triazolyl, 4- or 5-1,2,3-triazolyl, tetrazolyl, 2-, 3-, or 4-pyridinyl, 3-, 4-, or 5-pyridazinyl, 2-pyrazinyl, 2-, 4-, or 5-pyrimidinyl, 2-, 3-, 4-, 5-, 6-, 7-, or 8-quinolinyl, 1-, 3-, 4-, 5-, 6-, 7-, or 8-isoquinolinyl, 2-, 3-, 4-, 5-, 6-, or 7-indolyl, N-formyl-2-, 3-, 4-, 5-, 6-, or 7-indolyl, 2-, 3-, 4-, 5-, 6-, or 7-benzo[b]thienyl, 2-, 4-, 5-, 6-, or 7-benzoxazolyl, 2-, 4-, 5-, 6-, or 7-benzimidazolyl, or 2-, 4-, 5-, 6-, or 7-benzothiazolyl, unsubstituted or substituted by 1 to 2 substituents selected from the group consisting of lower alkyl, lower alkoxy, trifluoromethyl, nitro, halogen, CN, $SO_3H$, $SO_2NH_2$, $SO_2CH_3$, COOH, COO-lower alkyl, $CONH_2$, CO-lower alkyl, $NH_2$, NH-lower alkyl, N,N-di-lower alkyl, NH-aralkyl, N-di-aralkyl, and N,N-lower alkyl-aralkyl, or
heteroaryl-lower alkyl wherein heteroaryl is as defined above;

$R_2$ is a hydrogen atom or lower alkyl;

$R_3$ and $R_6$ are each independently hydrogen, lower alkyl or lower alkoxy, and $R_4$ and $R_5$ are each independently hydrogen, lower alkyl, lower alkoxy, trifluoromethyl, halo, $NO_2$, CN, $SO_3H$, $SO_2NH_2$, $SO_2CH_3$, $COOR_9$ in which $R_9$ is hydrogen or lower alkyl, $CONR_9R_{10}$ wherein $R_9$ and $R_{10}$ are each independently hydrogen or lower alkyl, or $NR_{11}R_{12}$ wherein $R_{11}$ and $R_{12}$ are each independently hydrogen, lower alkyl, aryl, wherein aryl is unsubstituted or substituted, heteroaryl as defined above or aralkyl, or a pharmaceutically acceptable acid addition or base salt thereof, with the following provisos:

(i) when B, C, D and E are defined as above where p is zero and $R_3$ to $R_6$ are as defined above, then R is halo-lower alkyl, phenyl or phenyl-lower alkyl in which phenyl is unsubstituted or substituted as defined above, heteroaryl as defined above or heteroaryl-lower alkyl, wherein heteroaryl is as defined above;

(ii) when B, C, D and E together with a carbon atom form a pyrrolidine optionally substituted by alkyl or carboxy-lower alkyl and $R_3$ and $R_6$ are as defined above, then R is halo-lower alkyl, aryl as defined above, aryl-lower alkyl, heteroaryl as defined above, or heteroaryl-lower alkyl wherein heteroaryl is as defined above;

(iii) when B, C, D and E together with carbon atoms form a piperidine R cannot be lower alkyl; and (iv) when B, C, D and E together with carbon atoms form an 1-aza-bicyclo[3.2,1]octane or 1-aza-bicyclo[2.2.2]octane R is not lower alkyl.

4. A compound according to claim 3 and of the formula wherein A is N;

B, C, D, E are $CH_2$ or $NR_{13}$ in which only one of B, C, D, or E is $NR_{13}$ wherein $R_{13}$ is hydrogen, lower alkyl, —$(CH_2)_mCO_2R_9$ in which $R_9$ is hydrogen or lower alkyl, or —$(CH_2)_m$—$NR_9R_{10}$ in which $R_9$ and $R_{10}$ are each independently hydrogen or lower alkyl and m is an integer of 0 to 6, and p is an integer from zero to 2;

R is lower alkyl, halo-lower alkyl, phenyl or phenyl-lower alkyl in which phenyl is unsubstituted or substituted by lower alkyl, lower alkoxy, trifluoromethyl, halo, $NO_2$, CN, $SO_3H$, $SO_2NH_2$, $SO_2CH_3$, $COOR_9$ in which $R_9$ is hydrogen or lower alkyl, $CONR_9R_{10}$ wherein $R_9$ and $R_{10}$ are each independently hydrogen, or $NR_{11}R_{12}$ wherein $R_{11}$ and $R_{12}$ are each independently hydrogen, lower alkyl, or aralkyl, heteroaryl wherein heteroaryl is 2- or 3-thienyl, 2- or 3-furanyl, 2- or 3-pyrrolyl, 2-, 4-, or 5-imidazolyl, 3-, 4-, or 5-pyrazolyl, 2-, 4-, or 5-thiazolyl, 3-, 4-, or 5-isothiazolyl, 2-, 4-, or 5-oxazolyl, 3-, 4-, or 5-isoxazolyl, 3- or 5-1,2,4-triazolyl, 4- or 5-1,2,3-triazolyl, tetrazolyl, 2-, 3-, or 4-pyridinyl, 3-, 4-, or 5-pyridazinyl, 2-pyrazinyl, 2-, 4-, or 5-pyrimidinyl, 2-, 3-, 4-, 5-, 6-, 7-, or 8-quinolinyl, 1-, 3-, 4-, 5-, 6-, 7-, or 8-isoquinolinyl, 2-, 3-, 4-, 5-, 6-, or 7-indolyl, N-formyl-2-, 3-, 4-, 5-, 6-, 7- or indolyl, 2-, 3-, 4-, 5-, 6-, or 7-benzo[b]thienyl, 2-, 4-, 5-, 6-, or 7-benzoxazolyl, 2-, 4-, 5-, 6-, or 7-benzimidazolyl, or 2-, 4-, 5-, 6-, or 7-benzothiazolyl, unsubstituted or substituted by 1 to 2 substituents selected from the group consisting of lower alkyl, lower alkoxy, trifluoromethyl, nitro, halogen, CN, $SO_3H$, $SO_2NH_2$, $SO_2CH_3$, COOH, COO-lower alkyl, $CONH_2$, CO-lower alkyl, $NH_2$, NH-lower alkyl, N,N-di-lower alkyl, NH-aralkyl, N-di-aralkyl, and N,N-lower alkyl-aralkyl, or heteroaryl-lower alkyl wherein heteroaryl is as defined above;

$R_2$ is a hydrogen atom or lower alkyl;

$R_3$ and $R_6$ are each independently hydrogen, lower alkyl or lower alkoxy, and $R_4$ and $R_5$ are each independently hydrogen, lower alkyl, lower alkoxy, trifluoromethyl, halo, $NO_2$, CN, $SO_3H$, $SO_2NH_2$, $SO_2CH_3$, $COOR_9$ in which $R_9$ is hydrogen or lower alkyl, $CONR_9R_{10}$ wherein $R_9$ and $R_{10}$ are each independently hydrogen or lower alkyl, or $NR_{11}R_{12}$ wherein $R_{11}$ and $R_{12}$ are each independently hydrogen, lower alkyl, aryl wherein aryl is unsubstituted or substituted, heteroaryl as defined above or aralkyl, or a pharmaceutically acceptable acid addition or base salt thereof, with the proviso that when p is 0, R is halo-lower alkyl, phenyl or phenol-lower alkyl in which phenyl is unsubstituted or substituted as defined above, heteroaryl as defined above or heteroaryl-lower alkyl wherein heteroaryl is as defined above.

5. A compound according to claim 3 and of the formula

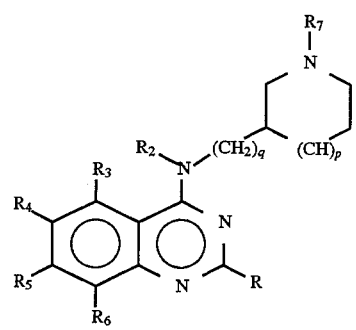

IV wherein q is 0, 1 or 2 and p is 0 or 1; R is lower alkyl, halo-lower alkyl, phenyl or phenyl-lower alkyl in which phenyl is unsubstituted or substituted by lower alkyl, lower alkoxy, trifluoromethyl, halo $NO_2$, CN, $SO_3H$, $SO_2NH_2$, $SO_2CH_3$, $COOR_9$ in which $R_9$ is hydrogen or lower alkyl, $CONR_9R_{10}$ wherein $R_9$ and $R_{10}$ are each independently hydrogen or $NR_{11}R_{12}$ wherein $R_{11}$ and $R_{12}$ are each independently hydrogen, lower alkyl, or aralkyl, heteroaryl as defined below or heteroaryl-lower alkyl wherein heteroaryl is defined below;

$R_2$ is a hydrogen atom or lower alkyl;

$R_3$ and $R_6$ are each independently hydrogen, lower alkyl or lower alkoxy, and $R_4$ and $R_5$ are each independently hydrogen lower alkyl, lower alkoxy, trifluoromethyl, halo, $NO_2$, CN, $SO_3H$, $SO_2NH_2$, $SO_2CH_3$, $COOR_9$ in which $R_9$ is hydrogen or lower alkyl, $CONR_9R_{10}$ wherein $R_9$ and $R_{10}$ are each independently hydrogen or lower alkyl, or $NR_{11}R_{12}$ wherein $R_{11}$ and $R_{12}$ are each independently hydrogen, lower alkyl, aryl wherein aryl is unsubstituted or substituted, heteroaryl wherein heteroaryl is 2- or 3-thienyl, 2- or 3-furanyl, 2- or 3-pyrrolyl, 2-, 4-, or 5-imidazolyl, 3-, 4-, or 5-pyrazolyl, 2-, 4-, or 5-thiazolyl, 3-, 4-, or 5- isothiazolyl, 2-, 4-, or 5-oxazolyl, 3-, 4-, or 5- isoxazolyl, 3- or 5-1,2,4-triazolyl, 4- or 5-1,2,3-triazolyl, tetrazolyl, 2-, 3-, or 4-pyridinyl, 3-, 4-, or 5-pyridazinyl, 2-pyrazinyl, 2-, 4-, or 5-pyrimidinyl, 2-, 3-, 4-, 5-, 6-, 7-, 8-quinolinyl, 1-, 3-, 4-, 5-, 6-, 7-, or 8-isoquinolinyl, 2-, 3-, 4-, 5-, 6-, or 7-indolyl, N-formyl-2-, 3-, 4-, 5-, 6-, 7- or indolyl, 2-, 3-, 4-, 5-, 6-, or 7-benzo[b]thienyl, 2-, 4-, 5-, 6-, or 7-benzoxazolyl, 2-, 4-, 5-, 6-, or 7-benzimidazolyl, or 2-, 4-, 5-, 6-, or 7-benzothiazolyl, unsubstituted or substituted by 1 to 2 substituents selected from the group consisting of lower alkyl, lower alkoxy, trifluoromethyl nitro, halogen, CN, $SO_3H$, $SO_2NH_2$, $SO_2CH_3$, COOH, COO-lower alkyl, $CONH_2$, CO-lower alkyl, $NH_2$, NH-lower alkyl, N,N-di-lower alkyl, NH-aralkyl, N-di-aralkyl, and N,N-lower alkyl-aralkyl, or aralkyl;

$R_7$ is hydrogen, lower alkyl, aralkyl, —$(CH_2)_mCO_2R_9$ in which $R_9$ is hydrogen or lower alkyl, or —$(CH_2)_m$—$NR_9R_{10}$ in which $R_9$ and $R_{10}$ are each independently hydrogen or lower alkyl and m is an integer of 1 to 6, or a pharmaceutically acceptable acid addition or base salt thereof; with the proviso that when p is 0, q is 1 or 2.

6. A compound of claim 5, wherein $R_4$ and $R_5$ are each independently hydrogen, trifluoromethyl, halo, $NO_2$, CN, $SO_3H$, $SO_2NH_2$, $SO_2CH_3$, $COOR_9$ in which $R_9$ is hydrogen or lower alkyl, $CONR_9R_{10}$ wherein $R_9$ and $R_{10}$ are each independently hydrogen or lower alkyl.

7. A compound of claim 6, wherein R is lower alkyl, halo-lower alkyl, phenyl or phenyl-lower alkyl in which phenyl is unsubstituted or substituted by lower alkyl, lower alkoxy or halo.

8. A compound of claim 7, wherein $R_4$ and $R_5$ are each independently hydrogen, halo or $NO_2$.

9. A compound of claim 8, wherein R is halo-lower alkyl.

10. A compound of claim 9 and selected from the group consisting of (1-ethyl-piperidin-3-yl)-(6-iodo-2-trichloromethyl-quinazolin-4-yl)-amine, [3-(6-iodo-2-trichloromethyl-quinazolin-4-ylamino)-piperidin-1-yl]-acetic acid, (1-ethyl-piperidin-3-yl)-(6-chloro-2-trichloromethyl-quinazolin-4-yl)-amine, (1-ethyl-piperidin-3-yl)-(6-nitro-2-trichloromethyl-quinazolin-4-yl)-amine, (1-ethyl-piperidin-3-yl)-(2-trichloromethyl-quinazolin-4-yl)-amine, (1-ethyl-piperidin-3-yl)-(7-chloro-2-trichloromethyl-quinazolin-4-yl)-amine, (1-ethyl-piperidin-3-yl)-(6-iodo-2-trifluoromethyl-quinazolin-4-yl)-amine, and (1-ethyl-pyrrolidin-2-yl-methyl)-(6-iodo-2-trichloromethyl-quinazolin-4-yl)-amine.

11. A compound of claim 8, and being selected from the group consisting of (1-ethyl-piperidin-3-yl)-(6-iodo-2-p-tolyl-quinazolin-4-yl)-amine, (1-ethyl-piperidin-3-yl)-[6-iodo-2-(4'-methoxy-phenyl)-quinazolin-4-yl]-amine, [2-(4'-chloro-phenyl)-6-iodo-quinazoline-4-yl]-(1-ethyl-piperidin-3-yl)-amine, and (1-ethyl-piperidin-3-yl)-(6-iodo-2-phenyl-quinazolin-4-yl)-amine.

12. A compound of claim 3 and being (1-aza-bicyclo[2.2.2]oct-3-yl)-(6-iodo-2-trichloromethyl-quinazolin-4-yl)-amine.

13. A method of treating cerebral ischemia comprising administering to a host suffering therefrom a therapeutically effective amount of a compound of the formula

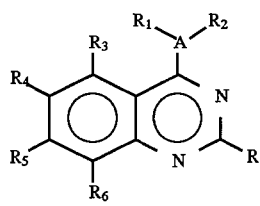

wherein A is N;
R is lower alkyl,
  halo-lower alkyl,
  aryl, wherein aryl is unsubstituted or substituted,
  aryl-lower alkyl, wherein aryl is defined above,
  heteroaryl, wherein heteroaryl is 2- or 3-thienyl, 2- or 3-furanyl, 2- or 3-pyrrolyl, 2-, 4-, or 5-imidazolyl, 3-, 4-, or 5-pyrazolyl, 2-, 4-, or 5-thiazolyl, 3-, 4-, or 5-isothiazolyl, 2-, 4-, or 5-oxazolyl, 3-, 4-, or 5-isoxazolyl, 3- or 5-1,2,4-triazolyl, 4- or 5-1,2,3-triazolyl, tetrazolyl, 2-, 3-, or 4-pyridinyl, 3-, 4-, or 5-pyridazinyl, 2-pyrazinyl, 2-, 4-, or 5-pyrimidinyl, 2-, 3-, 4-, 5-, 6-, 7-, or 8-quinolinyl, 1-, 3-, 4-, 5-, 6-, 7-, or 8-isoquinolinyl, 2-, 3-, 4-, 5-, 6-, or 7-indolyl, N-formyl-2-, 3-, 4-, 5-, 6-, or 7-indolyl, 2-, 3-, 4-, 5-, 6-, or 7-benzo[b]thienyl, 2-, 4-, 5-, 6-, or 7-benzoxazolyl, 2-, 4-, 5-, 6-, or 7-benzimidazolyl, or 2-, 4-, 5-, 6-, or 7-benzothiazolyl, unsubstituted or substituted by 1 to 2 substituents selected from the group consisting of lower alkyl, lower alkoxy, trifluoromethyl, nitro, halogen, CN, $SO_3H$, $SO_2NH_2$, $SO_2CH_3$, COOH, COO-lower alkyl, $CONH_2$, CO-lower alkyl, $NH_2$, NH-lower alkyl, N,N-di-lower alkyl, NH-aralkyl, N-di-aralkyl, and N,N-lower alkyl-aralkyl, or
heteroaryl-lower alkyl wherein heteroaryl is as defined above;
$R_1$ is a 5-7 membered saturated heterocyclic ring fused to a benzene ring, wherein the fused 5-7 membered saturated heterocyclic ring is selected from the group consisting of: dihydrobenzofuran, dihydroisobenzofuran, dihydrobenzothiophene, dihydroisobenzothiophene, indoline, isoindoline, chroman, isochroman, thiochroman, isothiochroman, tetrahydroquinoline, and tetrahydroisoquinoline, wherein said heterocyclic ring is attached directly to A or through an alkyl group linking A with the ring at a carbon atom, a 5-7 membered saturated heterocyclic ring optionally interrupted by a second heteroatom selected from nitrogen, oxygen and sulfur wherein the 5-7 membered heterocyclic ring is selected from the group consisting of: pyrrolidine, pyrrazolidine, imidazolidine, oxazolidine, thiaoxazolidine, piperidine, piperazine, morpholine, thiamorpholine, and homopiperidine, and wherein the second heteroatom atom is nitrogen, said second nitrogen atom may be substituted by alkyl, carboxyalkyl or lower alkylcarboxyalkyl and wherein the carbon atoms of the above 5-7 membered heterocyclic ring may be substituted independently by alkyl, amine, aminoalkyl, monoalkylaminoalkyl, dialkylaminoalkyl, carboxy, carboxyalkyl, alkylcarboxyalkyl, thio, thioalkyl, alkylthioalkyl, hydroxy, hydroxyalkyl, alkoxy or alkoxyalkyl wherein said heterocyclic ring is attached directly to A or through an alkyl group linking A with the ring at a carbon atom or 5,6 or 6,6-membered heterocyclic bicyclic rings, buying at least 1 heteroatom, selected from the group consisting of 1-aza-bicyclo[3,2,1]octane and 1-aza-bicyclo[2.2.2]octane said heterocyclic bicyclic rings being optionally substituted by
alkyl,
amino,
aminoalkyl,
monoalkylaminoalkyl,
dialkylaminoalkyl,
carboxy,
carboxyalkyl,
alkylcarboxyalkyl,
thio,
thioalkyl,
alkylthioalkyl,
hydroxy,
hydroxyalkyl,
alkoxy, or
alkoxyalkyl,
wherein said rings are attached directly to A or through an alkyl group linking A with the ring at a carbon atom;
$R_2$ is a hydrogen atom or lower alkyl;
$R_3$, $R_4$, $R_5$ and $R_6$ are each independently hydrogen, halo, lower alkyl, cycloalkyl, halo-lower alkyl, lower alkoxy, hydroxyalkyl, aminoalkyl, lower alkyl aminoalkyl, di-lower alkyl aminoalkyl, nitro, cyano, $SO_2NR_{11}R_{12}$, $SO_2R_9$, $CO_2R_9$, $CONR_{11}R_{12}$, or $NR_{11}R_{12}$ in which $R_{11}$ and $R_{12}$ are each independently hydrogen, lower alkyl, aryl as defined above, heteroaryl as defined above or aralkyl; or a pharmaceutically acceptable acid addition or base salt thereof in unit dosage form.

* * * * *

UNITED STATES PATENT AND TRADEMARK OFFICE
CERTIFICATE OF CORRECTION

PATENT NO. : 5,658,902
DATED : August 19, 1997
INVENTOR(S) : Kyunghye Ahn, Xue-Min Cheng, Annette Marian Doherty, Edward Faith Elslager, Brian Kornberg, Chitase Lee, Daniele Leonard, Sham Nikam, Leslie Morton Werbel It is certified that error appears in the above-indentified patent and that said Letters Patent is hereby corrected as shown below:

Column 38, line 27, delete "amine" and insert -- amino --.
at line 34, delete "buying" and insert -- having --.

Signed and Sealed this

Twelfth Day of October, 1999

Q. TODD DICKINSON

Attest:

Attesting Officer

Acting Commissioner of Patents and Trademarks